(12) United States Patent
Lee et al.

(10) Patent No.: US 8,586,370 B2
(45) Date of Patent: Nov. 19, 2013

(54) CHIMERIC PROTEIN, METHOD FOR MANUFACTURING THE SAME, NANO-SENSOR IN WHICH THE CHIMERIC PROTEIN IS FIXED, AND APPLICATION THEREOF

(75) Inventors: Jee Won Lee, Seoul (KR); Young Keun Kim, Seoul (KR); Moon Kyu Cho, Seoul (KR); Jin Seung Park, Incheon (KR); Eun Jung Lee, Goyang (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 13/225,088

(22) Filed: Sep. 2, 2011

(65) Prior Publication Data

US 2012/0149120 A1 Jun. 14, 2012

Related U.S. Application Data

(63) Continuation-in-part of application No. PCT/KR2010/000640, filed on Feb. 2, 2010.

(30) Foreign Application Priority Data

Mar. 6, 2009 (KR) .................. 10-2009-0019355

(51) Int. Cl.
*G01N 21/64* (2006.01)
*B82Y 15/00* (2011.01)

(52) U.S. Cl.
USPC ............................................... 436/86

(58) Field of Classification Search
USPC .................. 436/86; 435/69.7, 69.1, 41
See application file for complete search history.

(56) References Cited

FOREIGN PATENT DOCUMENTS

KR 1020040102012 12/2004

OTHER PUBLICATIONS

Fischlechner, M. et al., "Viruses as Building Blocks for Materials and Devices," Angew. Chem. Int. Ed., 46, pp. 3184-3193 (2007).
Lee, J.H. et al., "A Three-Dimensional and Sensitive Bioassay Based on Nanostructured Quartz Combined with Viral Nanoparticles," Adv. Funct. Mater., 20, pp. 2004-2009 (2010).
Nam, K.T., et al., "Virus-Enabled Synthesis and Assembly of Nanowires for Lithium Ion Battery Electrodes," Science, vol. 312, pp. 885-888, (May 12, 2006).
Park, J.S. et al., "A highly sensitive and selective diagnostic assay based on virus nanoparticles," Nature Nanotechnology, vol. 4, pp. 259-264 (Apr. 2009).
Werner, S. et al., "Immunoabsorbent nanoparticles based on a tobamovirus displaying protein A," PNAS, vol. 103, No. 47, pp. 17678-17683 (Nov. 21, 2006).
Yoo, P.J., et al., "Spontaneous assembly of viruses on multilayered polymer surfaces," Nature Materials, vol. 5, pp. 234-240 (Mar. 2006).
Kratz et al., "Native display of complete foreign protein domains on the surface of hepatitis B virus capsids", *Proc. Natl. Acad. Sci. USA*, vol. 96, pp. 1915-1920, Mar. 1999.
Office Action issued in Korean Patent Application No. 10-2011-0119198, dated Sep. 20, 2012.
Werner et al. "Immunoabsorbent nanoparticles based on a tobamovirus displaying protein A", *PNAS*, Nov. 21, 2006, vol. 103, No. 47, pp. 17678-17683.

*Primary Examiner* — Christine T Mui
(74) *Attorney, Agent, or Firm* — Edwards Wildman Palmer LLP

(57) ABSTRACT

There is provided a chimeric protein of capsid protein of Hepatitis B virus (HBV) and B domain of Staphylococcal protein A ($SPA_B$); a method for fabricating the same; the substrate and nanosensor immobilized with HBV-derived chimeric protein; and the use of the above nanosensor.

14 Claims, 25 Drawing Sheets

(a)  (b)

(c)  (d)

(A) N-HBVcAg(1-78)-H6-eGFP-HBVcAg(81-149)- C (B) N-HBVcAg(1-78)-H6-DsRed-HBVcAg(81-149)- C (C) N-HBVcAg(1-78)-H6-linker-eGFP-linker-HBVcAg(81-149)-C (D) N-HBVcAg(1-78)-H6-linker-DsRed-linker-HBVcAg(81-149)-C

FIG. 25

(A) Comparision of Fluorescence Intensities of eGFP Fusion Protein Nano Particiles

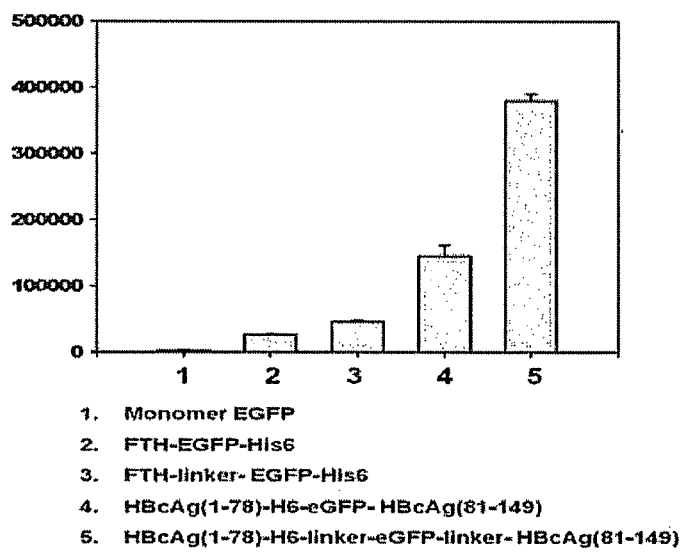

1. Monomer EGFP
2. FTH-EGFP-His6
3. FTH-linker-EGFP-His6
4. HBcAg(1-78)-H6-eGFP-HBcAg(81-149)
5. HBcAg(1-78)-H6-linker-eGFP-linker-HBcAg(81-149)

(B) Comparison of Fluorescence Intensities of DsRed Fusion Protein Nano Particles

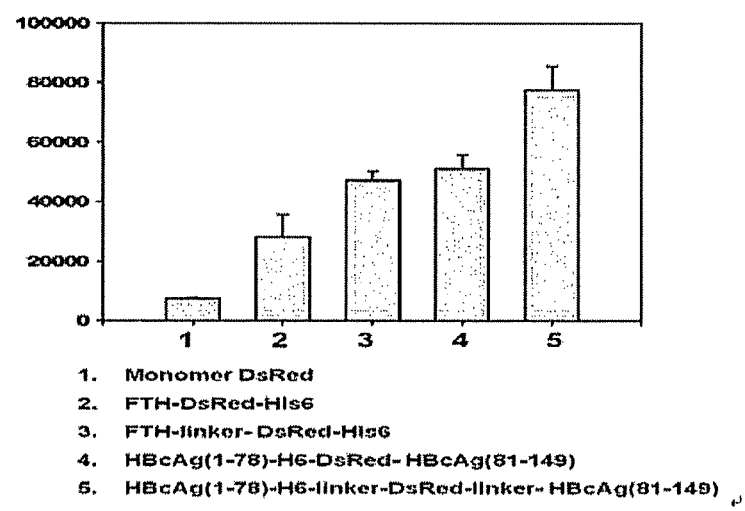

1. Monomer DsRed
2. FTH-DsRed-His6
3. FTH-linker-DsRed-His6
4. HBcAg(1-78)-H6-DsRed-HBcAg(81-149)
5. HBcAg(1-78)-H6-linker-DsRed-linker-HBcAg(81-149)

SEQUENCE LISTING

<160> NUMBER OF SEQ ID NOS: 34

<210> SEQ ID NO 1
<211> LENGTH: 45
<212> TYPE: DNA
<213> ORGANISM: Artificial Sequence
<220> FEATURE:
<223> OTHER INFORMATION: primer

<400> SEQUENCE: 1
catatgcatc accatcacca tcacgacatt gacccgtata aagaa         45

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
cccactccct ccgccaccgt cttccaaatt acttcccacc ca            42

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3
ctcgagagta ccgcctcccc cactccctcc gccacc                   36

<210> SEQ ID NO 4
<211> LENGTH: 39
<212> TYPE: DNA
<213> ORGANISM: Artificial Sequence
<220> FEATURE:
<223> OTHER INFORMATION: primer

<400> SEQUENCE: 4
ggatccggat ccggtggcgg agggtctggg ggaggcggt                39

<210> SEQ ID NO 5
<211> LENGTH: 48
<212> TYPE: DNA
<213> ORGANISM: Artificial Sequence
<220> FEATURE:
<223> OTHER INFORMATION: primer

<400> SEQUENCE: 5
ggcggagggt ctgggggagg cggttccagg ggattagtag tcagctat      48

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
aagcttttaa acaacagtag tttccggaag                          30

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ctcgaggcac cgaaagctga taac                                24

<210> SEQ ID NO 8
<211> LENGTH: 24
<212> TYPE: DNA

```
<213> ORGANISM: Artificial Sequence
<220> FEATURE:
<223> OTHER INFORMATION: primer

<400> SEQUENCE: 8
gaattcgtca gcttttggtg cttg                                          24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gaattcgcac cgaaagctga taac                                          24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ggatccgtca gcttttggtg cttg                                          24

<210> SEQ ID NO 11
<211> LENGTH: 189
<212> TYPE: DNA
<213> ORGANISM: Staphylococcus aureus

<400> SEQUENCE: 11
gcaccgaaag ctgataacaa attcaacaaa gaacaacaaa atgctttcta tgaaatctta   60
catttaccta acttaaatga agaacaacgc aatggtttca tccaaagctt aaaagatgac  120
ccaagccaaa gcgctaacct tttagcagaa gctaaaaagc taaatgatgc acaagcacca  180
aaagctgac                                                          189

<210> SEQ ID NO 12
<211> LENGTH: 234
<212> TYPE: DNA
<213> ORGANISM: Hepatitis B virus

<400> SEQUENCE: 12
atggacattg acccgtataa agaatttgga gcttctgtgg agttactctc tttttttgcct   60 tctgacttct ttccttctat tcgagatctc ctcgacaccg cctctgctct gtatcgggag  120
gccttagagt ctccggaaca ttgttcacct caccatacag cactcaggca agctattctg  180
tgttggggtg agttgatgaa tctggccacc tgggtgggaa gtaatttgga agac         234

<210> SEQ ID NO 13
<211> LENGTH: 78
<212> TYPE: PRT
<213> ORGANISM: Hepatitis B virus

<400> SEQUENCE: 13

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45
```

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp
65                  70                  75

<210> SEQ ID NO 14
<211> LENGTH: 207
<212> TYPE: DNA
<213> ORGANISM: Hepatitis B virus

<400> SEQUENCE: 14
tccagggaat tagtagtcag ctatgtcaac gttaatatgg gcctaaaaat cagacaacta    60
ttgtggtttc acatttcctg tcttactttt ggaagagaaa ctgttcttga gtatttggtg   120
tcttttggag tgtggattcg cactcctccc gcttacagac caccaaatgc ccctatctta   180
tcaacacttc cggaaactac tgttgtt                                        207

<210> SEQ ID NO 15
<211> LENGTH: 69
<212> TYPE: PRT
<213> ORGANISM: Hepatitis B virus

<400> SEQUENCE: 15

Ser Arg Glu Leu Val Val Ser Tyr Val Asn Val Asn Met Gly Leu Lys
1               5                   10                  15

Ile Arg Gln Leu Leu Trp Phe His Ile Ser Cys Leu Thr Phe Gly Arg
            20                  25                  30

Glu Thr Val Leu Glu Tyr Leu Val Ser Phe Gly Val Trp Ile Arg Thr
        35                  40                  45

Pro Pro Ala Tyr Arg Pro Pro Asn Ala Pro Ile Leu Ser Thr Leu Pro
    50                  55                  60

Glu Thr Thr Val Val
65

<210> SEQ ID NO 16
<211> LENGTH: 63
<212> TYPE: PRT
<213> ORGANISM: Staphylococcus aureus

<400> SEQUENCE: 16

Ala Pro Lys Ala Asp Asn Lys Phe Asn Lys Glu Gln Gln Asn Ala Phe
1               5                   10                  15

Tyr Glu Ile Leu His Leu Pro Asn Leu Asn Glu Glu Gln Arg Asn Gly
            20                  25                  30

Phe Ile Gln Ser Leu Lys Asp Asp Pro Ser Gln Ser Ala Asn Leu Leu
        35                  40                  45

Ala Glu Ala Lys Lys Leu Asn Asp Ala Gln Ala Pro Lys Ala Asp
    50                  55                  60

<210> SEQ ID NO 17
<211> LENGTH: 23
<212> TYPE: PRT
<213> ORGANISM: Artificial Sequence
<220> FEATURE:
<223> OTHER INFORMATION: Biotinated peptide

<400> SEQUENCE: 17

Met Ala Ser Ser Leu Arg Gln Ile Leu Asp Ser Gln Lys Met Glu Trp
1               5                   10                  15

Arg Ser Asn Ala Gly Gly Ser

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ctcgaggctc ctcagtctat t                                        21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
aagcttgttt tccatactga t                                        21

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
catatggaca ttgacccgta taaaga                                   26

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
ctcgaggtct tccaaattac ttccca                                   26

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
ggatcctcca gggaattagt agtcagc                                  27

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
aagcttttaa acaacagtag tttccggaag tgt                           33

<210> SEQ ID NO 24
<211> LENGTH: 39
<212> TYPE: DNA
<213> ORGANISM: Artificial Sequence
<220> FEATURE:

<223> OTHER INFORMATION: primer

<400> SEQUENCE: 24
ctcgagcatc accatcacca tcacgtgagc aagggcgag        39

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
ggatcccttg tacagctcgt ccatgcc        27

<210> SEQ ID NO 26
<211> LENGTH: 39
<212> TYPE: DNA
<213> ORGANISM: Artificial Sequence
<220> FEATURE:
<223> OTHER INFORMATION: primer

<400> SEQUENCE: 26
ctcgagcatc accatcacca tcacgacaac accgaggac        39

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
ggatccctgg gagccggagt ggcg        24

<210> SEQ ID NO 28
<211> LENGTH: 42
<212> TYPE: DNA
<213> ORGANISM: Artificial Sequence
<220> FEATURE:
<223> OTHER INFORMATION: primer

<400> SEQUENCE: 28
ggctctggtg gcggaagtgg gggtggcgtg agcaagggcg ag        42

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
agagccaccc ccacttccgc cacccttgta cagctcgtcc at        42

<210> SEQ ID NO 30
<211> LENGTH: 42
<212> TYPE: DNA
<213> ORGANISM: Artificial Sequence
<220> FEATURE:
<223> OTHER INFORMATION: primer

<400> SEQUENCE: 30
ggctctggtg gcggaagtgg gggtggcgac aacaccgagg ac        42

<210> SEQ ID NO 31

```
<211> LENGTH: 42
<212> TYPE: DNA
<213> ORGANISM: Artificial Sequence
<220> FEATURE:
<223> OTHER INFORMATION: primer

<400> SEQUENCE: 31
agagccaccc ccacttccgc caccctggga gccggagtgg cg                              42

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
ggtggcggaa gtgggggtgg ctctggtggc ggaagt                                     36

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
ctcgagcatc accatcacca tcacggtggc ggaagtggg                                  39

<210> SEQ ID NO 34
<211> LENGTH: 42
<212> TYPE: DNA
<213> ORGANISM: Artificial Sequence
<220> FEATURE:
<223> OTHER INFORMATION: primer

<400> SEQUENCE: 34
ggatccgcca cccccacttc cgccaccaga gccaccccca ct                              42
```

CHIMERIC PROTEIN, METHOD FOR MANUFACTURING THE SAME, NANO-SENSOR IN WHICH THE CHIMERIC PROTEIN IS FIXED, AND APPLICATION THEREOF

CROSS-REFERENCE TO RELATED APPLICATIONS

This application is a continuation-in-part of PCT/KR2010/000640 filed Feb. 2, 2010, which claims the benefit of Korean Application No. 10-2009-0019355 filed Mar. 6, 2009, the entire contents of which applications are incorporated herein by reference.

TECHNICAL FIELD

The present invention relates to a chimeric protein, a method for fabricating the same, a nanosensor immobilized with the same, and a use thereof.

BACKGROUND ART

In general, encapsidated viruses include a protein coat or "capsid" that is assembled to contain the viral nucleic acid. Many viruses have capsids that can be "self-assembled" from the individually expressed capsids, both within the cell the capsid is expressed in ("in vivo assembly") forming VLPs, and outside of the cell after isolation and purification ("in vitro assembly"). Ideally, capsids are modified to contain a target recombinant peptide, generating a recombinant viral capsid-peptide fusion. The fusion peptide can then be expressed in a cell, and, ideally, assembled in vivo to form recombinant viral or virus-like particles.

This approach has been met with varying success. See, for example, C Marusic et al., *J. Virol.* 75 (18):8434-39 (September 2001) (expression in plants of recombinant, helical potato virus X capsids terminally fused to an antigenic, HIV peptide, with in vivo formation of recombinant virus particles); F R Brennan et al., *Vaccine* 17 (15-16):1846-57 (9 Apr. 1999) (expression in plants of recombinant, icosahedral cowpea mosaic virus or helical potato virus X capsids terminally fused to an antigenic, *Staphylococcus aureus* peptide, with in vivo formation of recombinant virus particles).

U.S. Pat. No. 5,874,087 to Lomonossoff & Johnson describes production of recombinant plant viruses, in plant cells, where the viral capsids include capsids engineered to contain a biologically active peptide, such as a hormone, growth factor, or antigenic peptide. A virus selected from the genera Comovirus, Tombusvirus, Sobemovirus, and Nepovirus is engineered to contain the exogenous peptide encoding sequence and the entire engineered genome of the virus is expressed to produce the recombinant virus. The exogenous peptide-encoding sequence is inserted within one or more of the capsid surface loop motif-encoding sequences.

Attempts have been made to utilize non-tropic cells to produce particular virus like particles. See, for example, J W Lamb et al., *J. Gen. Virol.* 77 (Pt. 7):1349-58 (July 1996), describing expression in insect cells of recombinant, icosahedral potato leaf roll virus capsids terminally fused to a heptadecapeptide, with in vivo formation of virus-like particles. In certain situations, a non-tropic VLP may be preferable. For instance, a non-tropic viral capsid may be more accommodating to foreign peptide insertion without disrupting the ability to assemble into virus like particles than a native viral capsid. Alternatively, the non-tropic viral capsid may be better characterized and understood than a capsid from a native, tropic virus. In addition, the particular application, such as vaccine production, may not allow for the use of a tropic virus in a particular host cell expression system.

U.S. Pat. No. 6,232,099 to Chapman et al. describes the use of rod-shaped viruses to produce foreign proteins connected to viral capsid subunits in plants. Rod-shaped viruses, also classified as helical viruses, such as potato virus X (PVX) have recombinant peptides of interest inserted into the genome of the virus to create recombinant viral capsid-peptide fusions. The recombinant virus is then used to infect a host cell, and the virus actively replicates in the host cell and further infects other cells. Ultimately, the recombinant viral capsid-peptide fusion is purified from the plant host cells.

Meanwhile, there are many kinds of catalysts, such as a metal, a metal oxide, a solid acid, and the like. In addition, a producing method can largely be classified into an infiltration method (after immersing a support into a solution dissolving an active material, the active material is supported at the support by evaporating or adding a precipitate), an ion exchange method (an active material is exchanged to a support by contacting the support with the solution dissolving the active material), a precipitation method (passing through a activating process by precipitating the active material in a solution state), and the like. Of these, the present invention, which is a specific method out of the infiltration method of metal catalyst, uses a metal nickel as a catalyst because a nickel oxide (NiO) does not have an activity as a catalyst. In addition, since the nickel is easily made in desired shapes and desired sizes by using a nanotemplate as compared with the nickel oxide, it is often used to study a catalytic action of a metal wire, a metal thin film, a metal crystal, and the like by using the nickel. For example, a nickel nanohair structure is able to be biofunctionalized for the application in the field of biotechnology (BT). Especially, the exposed part of nickel nanowire can be used in a biosensor using the affinity of biomolecules-probe, antibody-antigen and biotin-avidin through a surface modification. Especially, the applicability of nickel nanowire can be greatly improved because the nickel can selectively bind with amine and histidine. In addition, it can also be possible to control the movement of nanostructure by using a magnetic property of nickel. However, it is extremely difficult to get the individual property from the AAO-free nanowire because an agglomeration phenomenon is generated due to a magnetic property and van der Waals forces.

Here, the nickel nanohair structure according to the present invention is a very useful nanomaterial for the chemical detection because it is uniform in height; the agglomeration phenomenon is prevented by being inside the nanotemplate; and it has a high density. Therefore, synthesizing method of a nanostructure is required for the study of the nickel nanohair structure.

Furthermore, the fabrication of nanostructures on transparent materials, such as quartz and glass, is under active investigation in a range of applications of sensor systems (P. Skladal, *Chem. Soc.* 2003, 14, 491; Z. Liu, M. D. Amiridis, *J. Phys. Chem.* B 2005, 109, 16866). In particular, quartz structures have been employed in various optical and optoelectrical applications on account of their good electrical insulation, absence of electromagnetic interference from other electric devices, excellent transparency for UV to visible light, good chemical stability, and high mechanical strength (A. Gopinath, S. V. Boriskina, N.-N. Feng, B. M. Reinhard, L. D. Negro, *Nano Lett.* 2008, 8, 2423; A. Dmitriev, C. Hagglund, S. Chen, H. Fredriksson, T. Pakizeh, M. Kall, D. S. Sutherland, *Nano Lett.* 2008, 8, 3893; T. Lohmuller, M. Helgert, M. Sundermann, R. Brunner, J. P. Spatz, *Nano Lett.* 2008, 8, 1429.).

In recent decades, plasma-related technologies have been employed for surface processing of various materials and for the production of nanostructured materials in both research and industrial settings.

Surface processing using plasma-related technologies can be categorized into two types: 1) surface modification, which results in a change in the chemical composition of a surface; and 2) selective dry-etching using reactive ionic species produced by a plasma, which makes it possible to fabricate nanometer-scale patterns on high-end materials. The latter technology, i.e., reactive ion etching (RIE), has been intensively employed in silicon-based technologies. Although masks are generally used to fabricate nanometer-scale patterns, RIE has been applied without a mask to fabricate micro- and nanostructures in some studies. However they utilized an undesirable artifact of etching, known as "RIE grass," that prevents clean delayering of integrated circuits (H. G. Craighead, R. E. Howard, J. E. Sweeney, D. M. Tennant, *J. Vac. Sci. Technol.* 1982, 20, 316; M. Gotza, B. Saint-Cricq, M. Dutoit, P. Jouneau, *Microelectron. Eng.* 1995, 27, 129; M. Gharghi, S. J. Sivoththaman, *Vac. Sci. Technol.* 2006, 24, 723; W. E. Vanderlinde, C. J. V. Benken, A. R. Crockett, *Proc. Soc. Photo. Opt. Instrum. Eng.* 1996, 2874).

RIE grass occurs as the result of the re-deposition of cathode materials (typically aluminum) or of polymerized complexes, such as fluorinated carbon onto the silicon or silicon oxide surface (M. Gharghi, S. J. Sivoththaman, *Vac. Sci. Technol.* 2006, 24, 723). With RIE grass formation alone, it is difficult to control the spacing of nanostructures, and therefore, there is a significant need for a new method to efficiently space nanostructures while avoiding the RIE grass formation.

The application of the etched quartz plates to biosensor systems that are subjected to detecting protein analytes requires immobilization of probe antibodies on the surface of nanostructured quartz plates, which is a key step to determine the sensitivity. The previous immobilization methods are based on direct antibody-surface binding that is performed using one of the following principles: 1) physical adsorption by hydrophobic interaction; 2) covalent linking between antibodies and a chemically activated solid surface; and 3) molecular affinity interactions, including specific binding of biotinylated antibodies to surface avidin (F. Rusmini, Z. Zhong, J. Feijen, *Biomacromol.* 2007, 8, 1775; W. Kusnezow, J. D. Hoheisel, *J. Mol. Recognit.* 2003, 16, 165; Y. Jung, Y. Jeong, B. H. Chung, *Analyst* 2008, 133, 697). Physical adsorption methods cause random/uncontrolled orientation of immobilized antibodies due to nonspecific binding of antibodies to the surface. Denaturation of antigen-binding domains (active sites) of antibodies may occur during the covalent linking of antibodies to chemically modified surfaces (F. Rusmini, Z. Zhong, J. Feijen, *Biomacromol.* 2007, 8, 1775; W. Kusnezow, J. D. Hoheisel, *J. Mol. Recognit.* 2003, 16, 165). Also, site-specific biotinylation of antibodies is almost impossible; that is, biotin may attach to any lysine residue(s) close to active sites of antibody and thereby interfere with the binding of target antigens to the active sites, and the random/uncontrolled orientation problems of antibodies still remains unsolved. These undesirable problems significantly reduce the sensitivity and specificity of biosensors (Y. Jung, Y. Jeong, B. H. Chung, Analyst 2008, 133, 697).

A plausible method to solve these problems is to use an antibody binding protein, such as bacterial Protein A or Protein G, which binds only to Fc domain of antibody. The approach does not require additional steps to chemically modify probe antibodies and therefore, can maintain intact active site of antibodies, allowing efficient and specific binding of antigens.

For an embodiment of the present invention, the present inventors propose the use of genetically engineered Hepatitis B virus (HBV) capsid particles that expose both biotinylated peptides and Staphylococcal Protein A in order to densely immobilize probe antibodies with well-organized orientation on nanostructured quartz.

Meanwhile, an early detection [Adams, J. E. et al. *Circulation* 88, 101-106 (1993); Adams, J. E., Schechtman, K. B., Landt, Y., Ladenson, J. H. & Jaffe, A. S. *Clin. Chem.* 40, 1291-1295 (1994); Thygesen, K., Alpert, J. S. & White, H. D. *J. Am. Coll.* Cardiol. 50, 2173-2195 (2007); Morrow, D. A. et al. *Clin. Chem.* 53, 552-574 (2007); Gibler, W. B. et al. *Ann. Emerg. Med.* 46, 185-197 (2005)] of Troponin I (Protein Marker) from a patient suffered with high risk acute myocardial infarction can reduce a risk rate of deaths from heart attack [Antman, E. M. et al. *N. Engl. J. Med.* 335, 1342-1349 (1996); Wu, A. H. B. & Jaffe, A. S. *Am. Heart J.* 155, 208-214 (2008); Benamer, H. et al. *Am. Heart J.* 137, 815-820 (1999); Heeschen, C., van den Brand, M. J., Hamm, C. W. & Simoons, M. L. *Circulation* 100, 1509-1514 (1999); Wong, G. C. et al. *Circulation* 106, 202-207 (2002)].

Most Troponin assays are currently based on the conventional Enzyme Linked Immunosorbent Assay (ELISA) and have detection limits in the nano- and picomolar range [Rosi, N. L. & Mirkin, C. A. *Chem. Rev.* 105, 1547-1562 (2005)].

The above information disclosed in this Background section is only for enhancement of understanding of the background of the invention and therefore it may contain information that does not form the prior art that is already known in this country to a person of ordinary skill in the art.

SUMMARY OF THE DISCLOSURE

An object of the present invention, which is created by a necessity as mentioned above to solve the above problems, provides a chimeric protein.

The other object of the present invention provides a method for fabricating the chimeric protein.

Another object of the present invention provides a substrate immobilizing the chimeric protein.

Another object of the present invention provides a three-dimensional nanostructure-based ultra-sensitive nanosensor immobilizing a specific material on the chimeric protein that is immobilized on the substrate.

Another object of the present invention provides a method for detecting a disease marker by using the three-dimensional nanostructure-based ultra-sensitive nanosensor.

In order to achieve the above objects, the present invention provides the chimeric protein that includes Staphylococcal protein A at a part of Hepatitis B virus capsid protein.

For an embodiment of the present invention, the chimeric protein according to the present invention is preferably B domain ($SPA_B$) of Staphylococcal protein A and capsid protein of Hepatitis B virus (HBV), and more preferably the protein includes 1-78 amino acid sequence region of Hepatitis B virus capsid protein, the region including Staphylococcal protein A, and 81-149 amino acid sequence region of the capsid protein, but is not limited thereto.

Furthermore, for an embodiment of the present invention, the chimeric protein preferably includes further a hexahistidine or biotinylated peptide sequence, but is not limited thereto.

In addition, the present invention provides a method for fabricating the chimeric protein, including a) obtaining a gene clone derived from Hepatitis B virus core protein (HBVcAg) gene; b) producing other clone for substituting HBVcAg site with B domain of Staphylococcal protein A ($SPA_B$) or inserting $SPA_B$ to HBVcAg site; c) producing an expression vector through a sequential ligation of the gene clones produced as mentioned above; and d) expressing the gene of chimeric protein by transforming the expressing vector to a host.

For an embodiment of the present invention, the producing method of the present invention preferably includes as follows: a) obtaining two gene clones that are derived from Hepatitis B virus core protein (HBVcAg) gene encoding synthesizes of N-NdeI-hexahistidine-HBVcAg(1-78)-G4SG4T-XhoI-C and N-BamHI-G4SG4-HBVcAg(81-149)-HindIII-C; b) producing other two clones, i.e., N-XhoI-$SPA_B$-EcoRI-C and N-EcoRI-$SPA_B$-BamHI-C in order to substituting P79A80 of HBVcAg with tandem repeat of 209-271 residues of B domain of Staphylococcal protein A ($SPA_B$); c) producing a plasmid expressing vector encoding the synthesis of N-$His_6$-HBVcAg(1-78)-$SPA_B$-$SPA_B$-HBVcAg(81-149)-C through a sequential ligation of the above four clones; and d) expressing the gene of chimeric protein by transforming the expression vector to a host, but it is not limited thereto.

The 'chimeric protein' or 'chimeric nanoparticle,' which is used as its widest mean, in the present invention means the protein or protein nanoparticles with various functionalities by combining a foreign biomaterial to the surface of the protein nanoparticles based on a genetic engineering and a protein engineering technique. Although HBV capsid of the present invention is used as a model virus scaffold for a surface display of $SPA_B$, other viruses or virus-like particles can be used for the production of chimeric protein or chimeric nanoparticles displaying a surface $SPA_B$.

Therefore, the present invention provides the substrate immobilizing HBV-derived chimeric protein as mentioned above.

For the present invention, the 'HBV-derived chimeric protein', which is used as its widest mean, means the proteins or protein nanoparticle with various functionalities by combining a foreign protein to HBV-derived protein.

For an embodiment of the present invention, the substrate preferably is used in the nanosensor, but is not limited thereto.

The 'substrate' used for the present specification may be a finely fabricated solid surface that is combined with functional molecules via covalent or non-covalent binding, and for example, includes silicon, Langmuir-Blodgett film, functionalized glass, germanium, ceramics, silicon, semiconductor raw material, PTFE, carbon, polycarbonate, mica, Mylar, plastic, quartz, polystyrene, gallium arsenide, gold, silver, metal, metal alloy, fabric, and their combinations capable of having functional group, such as amino, carboxyl, thiol or hydroxyl that are incorporated on their surfaces. Similarly, the surface of substrate may be large or small; and not always be uniform but should have a contacting surface (not always be single layer). The substrate may be porous, flat or non-flat. The substrate may be produced from itself or organic/inorganic molecules, and may include a second layer (for example, a biological material having a contact surface, or a substrate) that can contact with the organic or inorganic molecules.

For an embodiment of the present invention, the nanohair structure of the metal substrate is preferably produced by the method including, a) synthesizing a anodized aluminum oxide (AAO) nanotemplate of; b) depositing Ag on one side of the anodized aluminum oxide nanotemplate; c) depositing a nickel nanowire by using Pt as a counter electrode after putting the anodized aluminum oxide nanotemplate into the solution containing the nickel ion; d) planarizing the nickel nanowire through a process of Chemical Mechanical Polishing (CMP); and e) selective reactive ion etching (RIE) of anodized aluminum oxide nanotemplate.

For the method for producing the nanohair structure, the thickness of deposition of step b) preferably is 250~350 nm; the solution containing the nickel ion of step c) preferably is the mixture solution of nickel sulfate, nickel chloride and boric acid; and the process of reactive ion etching of step e) preferably is to etch the anodized aluminum oxide nanotemplate for 10 min in an etching rate of 0.25 µm/min using $BCl_3$ gas, but is not limited thereto.

For another embodiment of the present invention, preferably the quartz nanostructure is produced by coating a quartz wafer with poly(methyl methacrylate) and performing $O_2$ and $CF_4$ reactive ion etching (RIE), and the surface of quartz preferably is combined with avidin, but is not limited thereto.

The 'quartz nanostructure' used in the present invention means the quartz structure of nanopillar type that is formed to have a wide surface area through the reactive ion etching process.

Generally, the 'nanosensor' disclosed in the present invention means a device used for sensing molecules, specific compounds, and biomaterials (protein or DNA) in a fluid, such as gas or liquid; measuring a partial pressure and concentration of specific molecules; measuring the degree of vacuum of vacuum apparatus and vacuum chamber; or searching a site of gas leak in the vacuum apparatus and vacuum chamber.

In addition, the present invention provides a three-dimensional nanostructure-based nanosensor produced by adding more than one specific material selected from the group consisting of antibody, enzyme, protein, microorganism, nucleic acid, drug, and their combinations to the chimeric protein immobilized to the substrate and then by reacting more than one specific material as mentioned above with the surface of chimeric protein.

The term, 'three-dimensional nanostructure-based nanosensor' used in the present invention means the sensor, of which its sensitivity for detecting a specific disease marker protein, and the like is maximized through the combination of three-dimensional protein nanoparticle probe material and three-dimensional nanostructure.

In addition, the present invention provides a detection method of a disease marker, including the reaction of a sample to be diagnosed with the three-dimensional nanostructure-based nanosensor.

For an embodiment of the present invention, the sample may be preferably blood, serum, urea, saliva, sputum or nasal discharge, but is not limited thereto.

The term, 'biomarker' or 'disease marker' used in the present invention generally is molecules, that is, gene (or nucleic acid encoding the gene), protein, carbohydrate structure or glycolipid, and can anticipate or show the condition of subject, from which the sample is collected, by detecting its expression on the sample or sample derived from the mammal tissue or cell using the standard method in the industry. The activation of disease including the deterioration and improvement of the conditions of patients can be distinguished by the level of the disease marker. Therefore, for an embodiment, the useful disease marker in the present invention may be preferably Troponin I or an enterotoxin, but is not limited thereto. In addition, monitoring the disease markers makes it possible to be used in rapid diagnosis or determination of the patients' prognosis.

The term, "vector" used in the present specification refers to a nucleic acid molecules that can carry other nucleic acid incorporated in the above vector. One type of vector, "plasmid", one type of vector, refers to a circular double-strand DNA loop that can be possible to be linked with an additional DNA fragment therein. Other type of vector may be a virus vector, and at this time, an additional DNA fragment can be inserted in the virus genome. A specific vector can be self-replicated in a host cell (For example: a bacterial vector having a replication origin of bacteria and an episomal mammalian vector). On the other hand, some vectors (For example: non-episomal mammalian vector) can be integrated into the genome of host cells to be replicated. In addition, a specific vector can control the expression of related genes. The vector is called as "a recombinant expression vector" (or simply "expression vector") in the present specification. In general, the expression vector used in the recombination DNA technique may be frequently a type of plasmid. Since the plasmid is a type of most generally used vector, the "plasmid" and "vector" can be interchangeably used in the present specification. However, the present invention includes the expression vectors of other types, such as the virus vector having the same function (For example: replication defective retrovirus, adenovirus and adeno-related virus).

The term, "recombinant host cell" (or simply "host cell") used in the present specification refers to the cell introduced with the recombinant expression vector. The term should be understood to include a specific subject cell as well as a progeny thereof. Since there may be a specific modification in the next generation due to the environmental effect or mutant, the progeny should be included in the range of the term, "host cell" used in the present specification, even though it may be substantially not the same with its parent cell.

The above and other features and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF THE DRAWINGS

The above and other aspects, features and other advantages of the present invention will be more clearly understood from the following detailed description taken in conjunction with the accompanying drawings, in which:

FIG. 1(a) shows the synthesize of anodized aluminum oxide nano template; FIG. 1(b) shows the deposition of conductive layer (Ag, 250~350 nm) by E-beam evaporation; FIG. 1(c) shows the synthesize of nanowires inside the nano template; FIG. 1(d) shows the planarization process of nanowires and nano template; and FIG. 2(e) shows a selective etching process of nano template for nanohair wire structure.

FIGS. 1(a) and (b) show floor plans that are planarized by chemical mechanical polishing (CMP) process;

FIGS. 2(c) and (d) show cross-sectional diagrams that are planarized by the chemical mechanical polishing process; and FIGS. 2(e) and (f) show cross-sectional diagrams of nickel nanohair wire structure by selective reactive ion etching (RIE) process of nano template.

FIG. 3 shows schematic and TEM images of native hepatitis B virus (HBV) capsid particles and chimeric nanoparticles synthesized in $E.\ coli$ and FIG. 4 shows schematic of the diagnostic system performed in a 96-well microplate and the assay principle in detail. Briefly, antibodies that recognize the disease marker (Troponin I in this case) bind to the chimeric nanoparticle and are oriented in a specific way. Troponin I binds to the antibodies and detection is achieved with secondary antibodies conjugated with quantum dots.

FIG. 5 shows that the conventional ELISA assay could not detect Troponin I at concentrations lower than 0.1 nM, and FIG. 6 shows that the assay using chimeric nanoparticles and nickel nanohairs shows attomolar sensitivities in both PBS and human sera. "Control" refers to the experiment in which only quantum-dot-secondary antibodies were added to the nickel nanohair surface, which was covered with a sufficient amount of chimeric nanoparticles (30 nM in PBS buffer 50 μl).

FIG. 7 shows Four-step protocol for washing and reusing the nickel nanohairs for detection.

FIG. 8 shows the consecutive assays of eight different Troponin I (TnI) samples using three separate systems, showing good reproducibility. A, B, C, D, dotted and solid arrows, and PL1/PL2 correspond to those in FIG. 7. Black areas represent net PL increase.

FIG. 9 shows that chimeric nanoparticles immobilized on PVDF membranes show similar detection sensitivities in both PBS and human sera.

FIG. 10 shows that antibodies immobilized directly on the PVDF membranes show significantly lower sensitivities than those immobilized on chimeric nanoparticles.

FIG. 12 shows assays with antibodies attached to chimeric nanoparticles, but not those immobilized directly on PVDF membranes, could detect Troponin I in a sample diluted 1,000 times. 74/M and 75/F represent the age and gender of the AMI patients.

FIG. 16 shows schematic illustration and transmission electron microscopy (TEM) image of the biotinylated viral nanoparticles derived from HBV capsid particles, which were synthesized in E. coli.

FIG. 17 shows schematic illustration of 3D assay system and principle used in the present invention for the detection of disease-specific protein markers (e.g., ETEC enterotoxin LT-B in this case). [The structures of the capsid particle and dimer cluster spike of HBV are available from the Protein Data Bank (PDB ID: 1QGT)].

FIG. 18 shows results of LT-B assay and negative control experiments that were performed using either the 3D assay system (solid bar) or plane quartz-based assay system (dashed bar). ("Net photoluminescence" represents photoluminescence value that is obtained by subtracting background photoluminescence signal of bare quartz surface from actual photoluminescence signal measured).

FIG. 19 shows schematic illustration of four negative control experiments.

FIG. 25 shows graphs showing the fluorescence determinant of HBV capsid-derived chimeric fluorescence nanoparticles produced.

DETAILED DESCRIPTION OF THE DISCLOSURE

Figure 1:
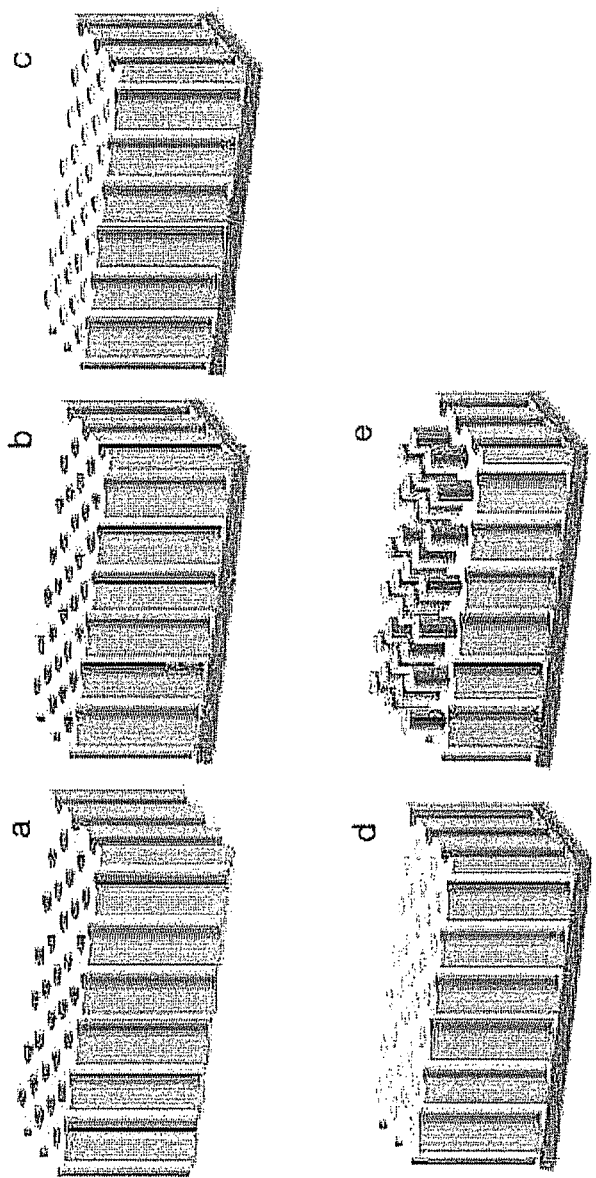
FIG. 1 shows a process mimetic diagram of a fabrication method of nanohair wire structure.
Figure 2:
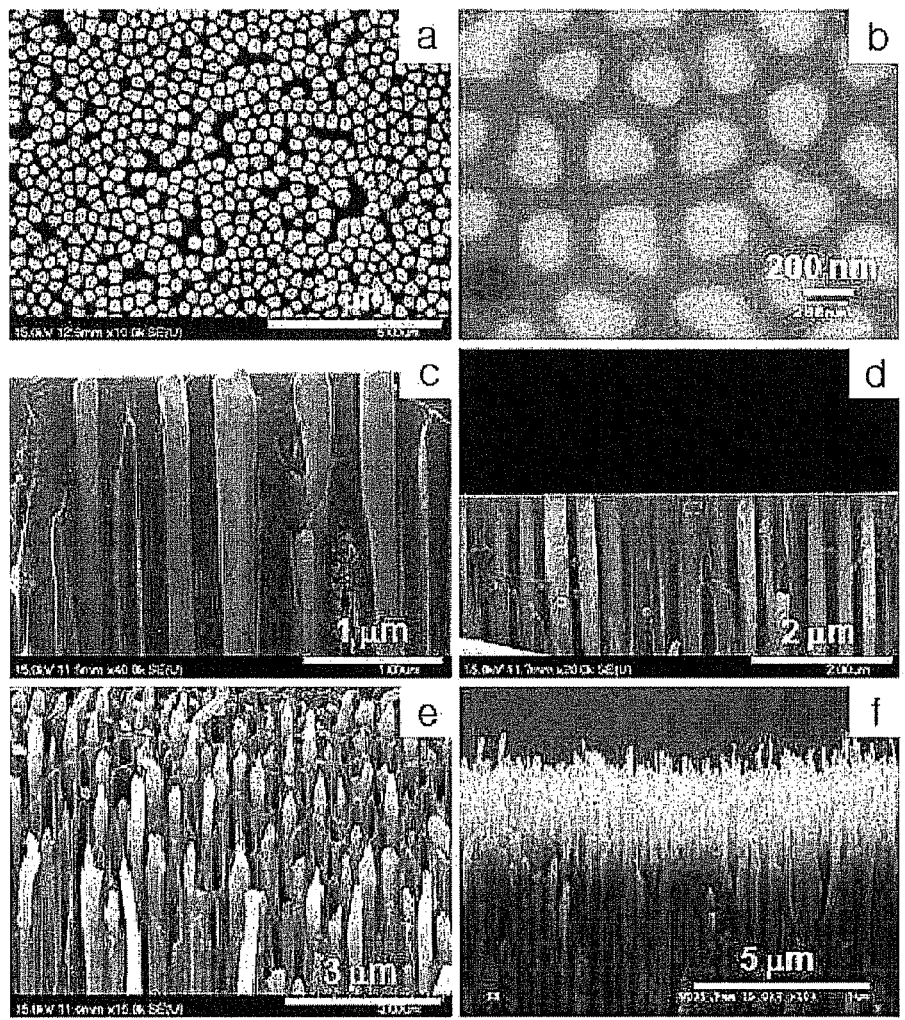
FIG. 2 shows Field Emission-Scanning Electron Microscope (FE-SEM) images of nickel nanohair wire structure according to Example of the present invention.

Hereinafter, the present invention will be described with embodiments of the present invention. Embodiments of the method for synthesizing a nickel nanohair wire structure will be described with Examples of the present invention.

Example 1 of the present invention relates to a method for forming nanohair structure having an exposed nanowire structure on AAO nanotemplate after synthesizing the nanowire having one-dimension in AAO (anodized aluminum oxide) nanotemplate. An object of the present invention is to provide a bio nano catalyst material that can be applied in vitro by using the nanowire as a catalyst for the application in the biochemical field.

The technique according to Example 1 of the present invention is based on an electrochemistry, and relates to a producing method that would allow the mass production of a catalyst at low cost, in which the catalyst can increase the reaction velocity, that is, can make the reaction of low activation energy by contacting with a reactant. The technique can be implemented by exposing the nickel nanowire through a selective isotropy reactive ion etching (RIE), after synthesizing the nickel nanowire in AAO nanotemplate produced by an electroplating method.

A producing process of the nickel nanostructure according to the present invention includes regularly planarizing the heights of nanowire and AAO through a chemical mechanical polishing (CMP), after synthesizing the nanowire in AAO nanotemplate by using an electrochemical method. AAO nanotemplate of the sample resulted from the above steps is selectively etched through an etching process by using a reactive ion etching (RIE) apparatus. The nanohair structure (Ni Nanohair structure) exposed on the final AAO nanotemplate like hairs can be synthesized through the processes as mentioned above. The nanohair structure implemented as mentioned above does not have an agglomeration phenomenon of nanowires, and has very high density ($10^6$ number/$cm^2$) and a regular height (max. 60 μm) so that its applicability is largely increased as a catalyst in the biochemical and environmental fields.

The 'chemical mechanical polishing' is one of the methods generally used in the process of planarization, and includes pressing the active surface to the rotating polishing pad and then introducing a polishing and/or chemical reaction solution that is known as "slurry" on the polishing pad. The mechanical effect of pressure is applied through the polishing pad, and the chemical reaction caused by the input of slurry allows the materials to be selectively removed from the active surface, resulting more uniform surface. Typically, deionized water with high purity is applied to the polishing solution as base, and a particle and/or chemical additive having the effect of polishing is added therein. The more information about the chemical mechanical polishing, the slurry, and the like is disclosed in U.S. Pat. Nos. 6,914,001 and 6,887,137.

The 'Troponin I' disclosed in the specification of the present invention is a type of proteins found in the blood of patients suffered from a cardiac infarction, and when detecting in the existence of Troponin I, it can be judged to have a disorder of heart.

The 'nickel nanohair structure' disclosed in the specification of the present invention is the structure of exposed nanowire by selective etching of AAO nanotemplate using the reactive ion etching (RIE) process, and equalizing the length of nanowire by using the chemical mechanical planarization (CMP) process, after synthesizing nickel nanowire in AAO nanotemplate.

The 'PVDF membrane (poly(vinyl difluoride) membrane)' disclosed in the specification of the present invention is the polymer membrane having small pores and hydrophobic property (no compatibility with water), and the present invention used the membrane having the pore of 450 nm size, in which the membrane has the property that allows the surface thereof to easily well take the nanoparticles.

The 'bio nano probe' disclosed in the specification of the present invention is used as a sensor material that is integrated with the target detection probe on the protein nanoparticles.

The present inventors showed that combining the three-dimensional nanostructure including the nickel nanohair and virus nanoparticles that are designed to have a dual affinity for antibodies and nickel can detect at low level of Troponin, i.e., $10^6$~$10^7$ in human serum as compared with using the typical ELISA assay [Hirsch, L. R., Jackson, J. B., Lee, A., Halas, N. J. & West, J. Anal. Chem. 75, 2377-2381 (2003); Nam, J. M., Park, S. J. & Mirkin, C. A. J. Am. Chem. Soc. 124, 3820-3821 (2002); Niemeyer, C. M. & Ceyhan, B. Angew. Chem., Int. Ed. 40, 3685-3688 (2001); Chien, R. J. et al. Proc. Natl. Acad. Sci. 100, 4984-4989 (2003) Wang, J., Polsky, R., Merkoci, A. & Turner, K. L. Angew. Chem., Int. Ed. 43, 2158-2161

(2004)] in the present invention. The virus nanoparticles help the orientation of antibodies for the maximum capture of Troponin marker. As a large number of Troponin markers are bound to the densely immobilized antibodies on the nanostructure, the sensitivity of detection is largely increased. The nickel nanohair is able to be used repeatedly and reproducibly to distinguish the healthy serum from the patient serum. The present inventors anticipate that other virus nanoparticles can be used in diagnosis assay with high similar sensitivity to other various protein markers.

For the present invention, the present inventors synthesized Hepatitis B virus (HBV) capsid-derived nanoscale particles (hereinafter, called as to chimeric nanoparticles), at the surface of which the B domains of Staphylococcal protein A ($SPA_B$) [Gouda, H. et al. Biochemistry 37, 129-136 (1998); Deisenhofer, J. Biochemistry 20, 2361-2370 (1981)] with a specific affinity for the Fc domain of immunoglobulin G are displayed with high density.

Figure 4:
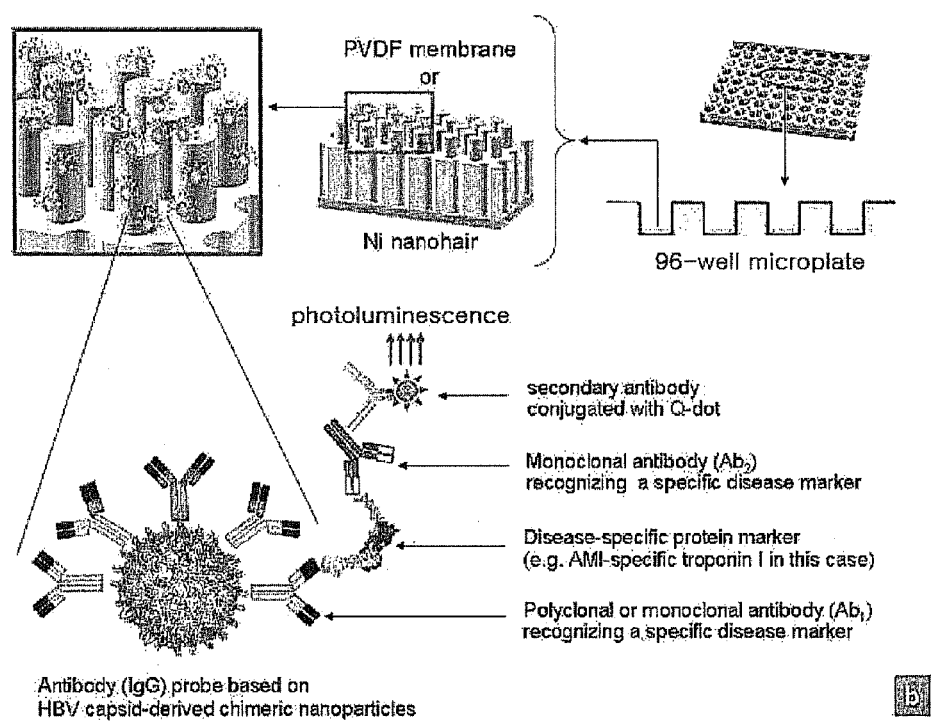

Hepatitis B virus is surrounded by an envelope HBV surface antigen ("HBsAg"); consists of an internal nucleocapsid including HBV core protein ("HBcAg"), virus polymerase, and virus DNA. It is a blood-mediated virus containing a small partially double-strand DNA genome with four widely overlapped open reading frame. The virus envelope includes three different, but related long (L), meddle (M), and short (S) surface antigen proteins. They share a common carboxy-terminal portion, but include different amino terminals, and are generated by the different starting codons in the continuous open reading frame.

The long polypeptide (L polypeptide) consists of pre-S1, pre-S2, and S region. As a product of completely translated structure, it contains pre-S1 domain of 108 amino acids (or 199 amino acids depending on a type of subunit of virus), followed by pre-S2 of 55 amino acids, and the S polypeptide region of 226 amino. While the middle-length polypeptide (M polypeptide) includes pre-S2 domain on the amino terminal of following S region, S polypeptide that is the most abundant type consists of only S region. The pre-S region is considered to play an important rule in both the virus assembly and the attachment to the host cell. S type is more abundant as compared with M and L types of HBsAg in the virus, and generates in both of the glycosylated type and non-glycosylated type [V. Bruss and D. Garem, "Role of Envelop Protein On Assembling Hepatitis B Virus", *Proc. Natl. Acad. Sci*. USA, 88, pp. 1059-63 (1991); V. Bruss et al., "Modification After Translation of Hepatitis B Virus Large Envelope Protein on a dural", *EMBO J.,* 13, pp. 2273-79 (1994); A. R. Neurath et al., "Screening and chemically Synthesizing Host Cell Receptor Binding Site of Hepatitis B Virus", *Cell,* 46, pp. 429-36 (1986); K. Ueda et al., "Three Envelope Proteins of Hepatitis B Virus: Large S, Middle S, and Main S Protein Required for forming Dane Particles", *J. Viol,* 65, pp. 3571-29 (1991)]. A specific correlation between the inner surface of envelope and outer surface of core may be considered to induce an accurate assembly of virus and stabilize the particle produced.

HBV core protein can be effectively expressed in *E. coli* [M. Pasek et al., "Hepatitis B Virus in *E. coli* and Expression thereof", *Nature,* 282, pp. 575-79 (1979)]. The protein is assembled in an icosahedral shell with two sizes containing 180 (T=3) or 240 (T=4) subunit [R. A. Crowther et al., "3D Structure of Hepatitis B Virus Core Particle Determined by an Electron Microscope", *Cell,* 77, pp. 943-50 (1994)]. The subunits are assembled into dimers, and each of dimers form spike projected from the surface of shell. Using an electron cryomicroscopy and an image processing, a map of T=4 shell has been recently made at 7.4 A resolution from the images of at least 6000 individual particles [B. Bottecher et al., "Measurement of Folding of Core Protein of Hepatitis B Virus by Electron Cryomicroscopy", *Nature,* 386, pp. 88-91 (1997)]. It was shown that a folding of polypeptide chain is very different from the virus capsid that is previously solved, and is generally α-helix. Each dimer spike is formed by a long pair of α-helix hairpins that consists of one from each monomer of dimer [Bottcher et al., (1997); J. F. Conway et al., "Visualization of 4-helix Bundle on Hepatitis B Virus by Electron Cryomicroscopy", *Nature,* 386, pp. 91-94 (1997)]. A numbering plan of Overlapping Amino Acid Sequence on Folding [Bottcher et al., (1997)] makes Main Immuno Dominant Reagion of HBV Core Protein [J. salfeld et al., "Functional Domain and Epitope on E Antigen and Core Antigen from Hepatitis B Virus", *J. Virol,* 63, pp. 798-800 (1989); M. Sallberg et al., "Characterization of Linear Binding Region For Monoclone Antibody to Hepatitis B Virus Core Antigen", *J. Med. Viol*. 33, pp. 248-52 (1991)] to locate around amino acid 78-82 on the terminal of spike.

Meanwhile, the HBV core protein, consisting of four long alpha-helix bundles (FIG. 3), when expressed in bacteria, assembles into core-shell particles that closely resemble the native capsid structure of virus [Bottcher, B., Wynne, S. A. & Crowther, R. A. *Nature* 386, 88-91 (1997); Crowther, R. A. et al. *Cell* 77, 943-950 (1994)]. Through the electron cryomicroscopy analysis, Bottcher and colleagues demonstrated that a single HBV core protein truncated after residue 149 forms the core-shell particles that contain 240 subunits and have an overall diameter of 36 nm [Bottcher, B., Wynne, S. A. & Crowther, R. A. *Nature* 386, 88-91 (1997)]. The dimer clustering of the subunits produces spikes on the surface of the shell particle, and the immunogenic epitope is located at the tips of prominent surface spikes (FIG. 3). The surface-exposed spike tip corresponds to the loop segment consisting of the residues from D78 to D83 of the single core protein. The present inventors made that the P79A80 in the loop segment was replaced with the tandem repeated $SPA_B$ sequences (NCBI nucleotide accession No. M18264 nucleotide sequence 625-813, Sequence No. 11), which were subsequently exposed on the surface of the synthesized chimeric nanoparticles with high density (FIG. 3). In the chimeric nanoparticle synthesis, the present inventors also added the hexahistidine sequence to the N-terminus of the truncated HBV core protein so that the chimeric nanoparticles would have a strong affinity for nickel (FIG. 3). Transmission electron microscopy (TEM) image analysis (FIG. 3) revealed that the HBV capsid-derived chimeric nanoparticles that were expressed in *E. coli* assembled into spherical nanoparticles with a nearly native diameter. Consequently, the chimeric nanoparticles have a dual affinity for the Fc domain of antibodies (IgG) and nickel. These viral particles can display on their surface various peptides and proteins that are used for detecting and/or quantifying biomolecules of interest.

As illustrated in FIG. 4, a three-dimensional assay system was developed by combining the chimeric nanoparticles with a nickel nanohair structure or porous membrane, and then adding antibodies to specifically capture protein markers. For the present invention, the term 'nanohair' refers to an array of nanowires in which some wires are exposed to the air, the rest being embedded in the body of a supporting organic or inorganic template (FIG. 4). In these structures, the air-exposed portion of the nanowires has a greatly increased surface-to-volume ratio.

When antibodies are added to the chimeric nanoparticles that are already attached to the nickel nanohair surface as a result of the affinity interaction between the hexahistidin and nickel (FIG. 3), the Fc domain of antibody (IgG) is specifically bound to the surface SPA$_B$ of the chimeric nanoparticles, and hence the antigen-specific variable domains of IgG are fully accessible to protein markers. Consequently, as illustrated in FIG. 4, the efficient three-dimensional assay system was developed with the following significant advantages: (i) maximum accessibility of protein markers to antibodies, enabled both by the controlled orientation of the antibodies and the three-dimensional manner of protein capture, and (ii) a dramatically increased density and ratio of antibodies to protein markers on the three-dimensional nanohair surface. The captured markers were detected by sensing photoluminescence emitted by quantum dots conjugated to the secondary antibodies (FIG. 4).

Figure 5:
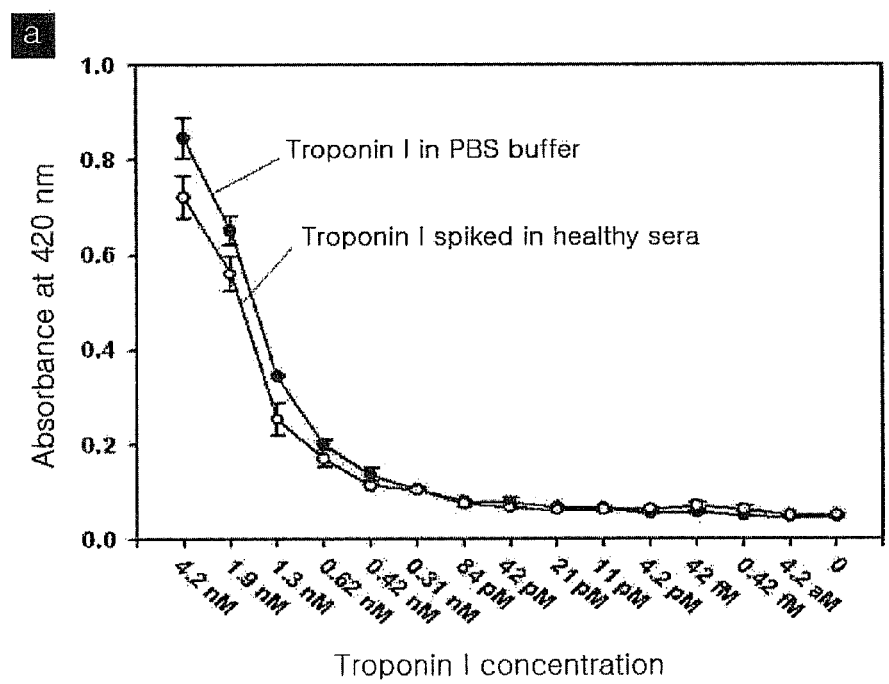
FIGS. 5 and 6 show the detection of Troponin I.
Figure 6:
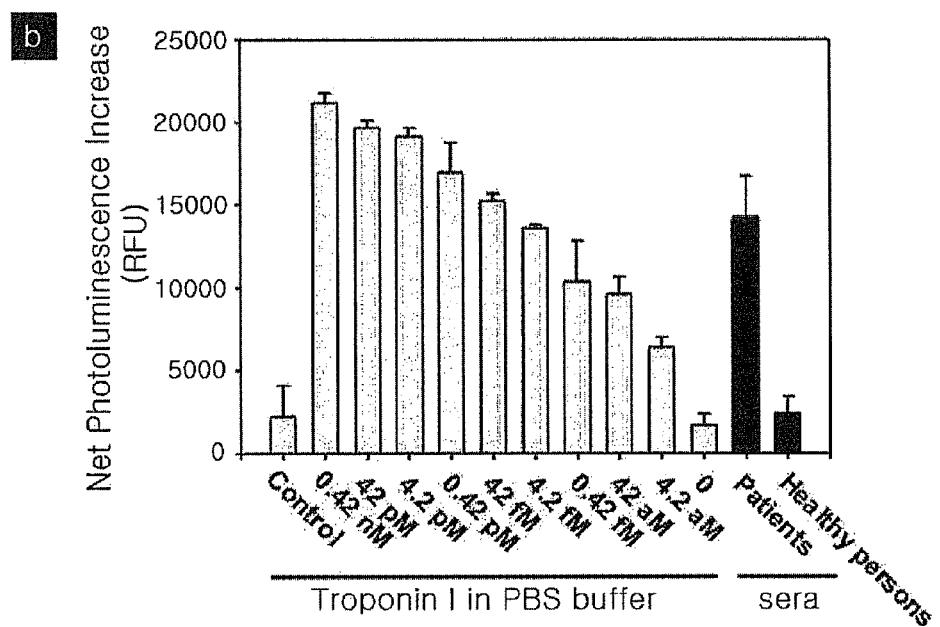
Figure 7:
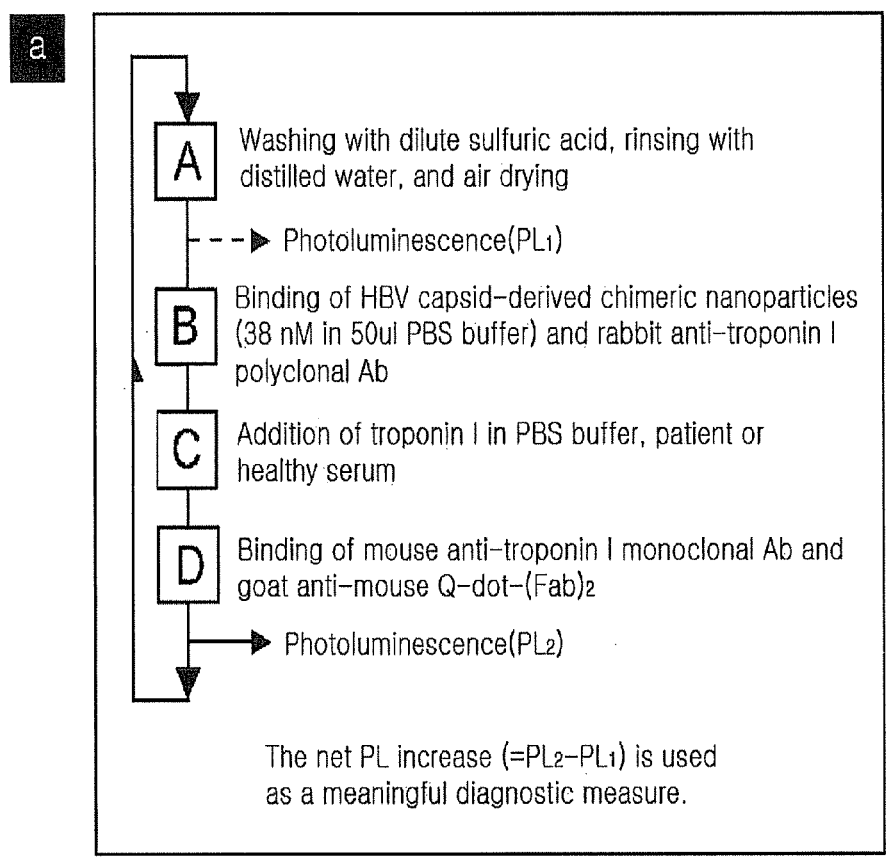
FIGS. 7 and 8 show a washable and reusable assay system.
Figure 8:
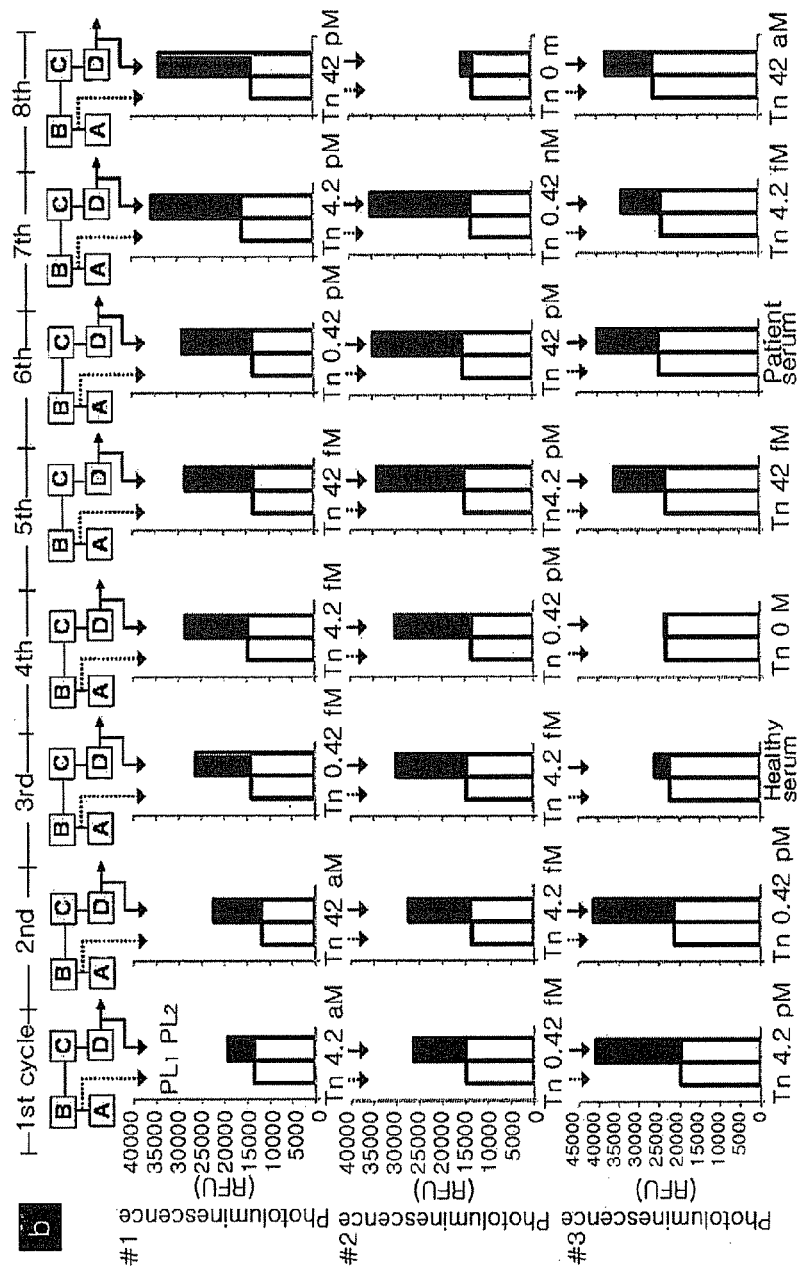
Figure 13:
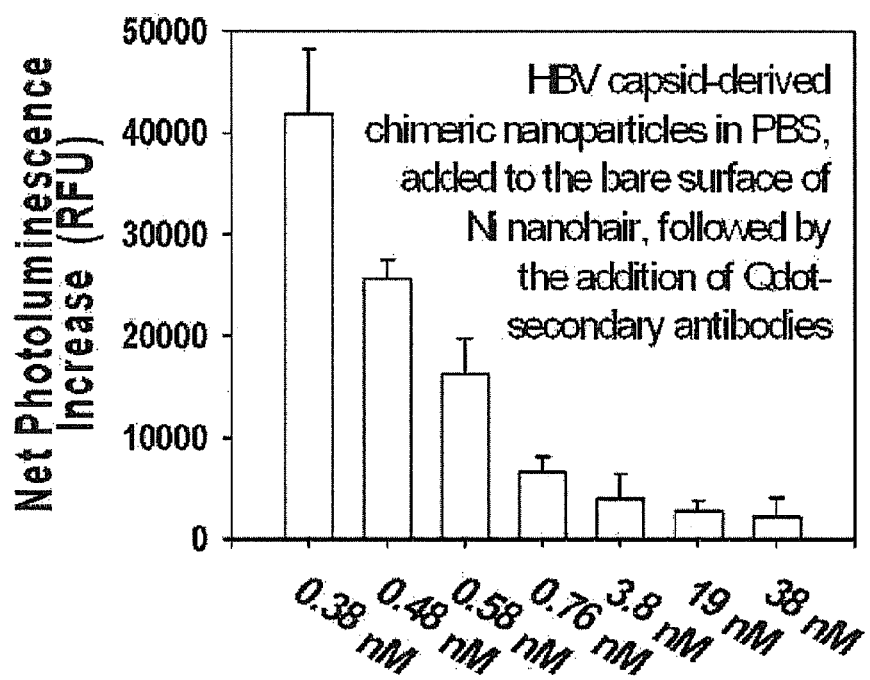
FIG. 13 shows a graph for determining an amount of HVB capsid-derived chimeric nanoparticles added to bare nickel surface, preventing the binding of non-specific quantum-dot-secondary antibodies to the nickel surface.

From FIG. 5, it is clear that the ELISA-based assay (see Examples) did not detect Troponin I (in PBS buffer or healthy sera) at concentrations lower than about 0.1 nM, but gave highly reproducible signals at each Troponin I concentration. Using the chimeric nanoparticles and nickel nanohair system developed in the present invention, the sensitivity was surprisingly boosted to low $10^{-18}$ level (FIG. 6), which represents about 100,000-fold higher sensitivity than the highest level (0.25 pM) reported to date [Apple, F. S., Smith, S. W., Pearce, L. A., Ler, R. & Murakami, M. M. *Clin. Chem.* 54, 723-728 (2008)] and also $10^6$~$10^7$ greater sensitivity than current ELISA assays [Rosi, N. L. & Mirkin, C. A. *Chem. Rev.* 105, 1547-1562 (2005); Hirsch, L. R., Jackson, J. B., Lee, A., Halas, N. J. & West, *J. Anal. Chem.* 75, 2377-2381 (2003); Nam, J. M., Park, S. J. & Mirkin, C. A. *J. Am. Chem. Soc.* 124, 3820-3821 (2002); Niemeyer, C. M. & Ceyhan, B. DAngew. *Chem., Int. Ed.* 40, 3685-3688 (2001); Chien, R. J. et al. *Proc. Natl. Acad. Sci.* 100, 4984-4989 (2003); Wang, J., Polsky, R., Merkoci, A. & Turner, K. L. Angew. *Chem., Int. Ed.* 43, 2158-2161 (2004)]. As shown in the binding of the chimeric nanoparticles (i.e., in the step B of FIG. 7), to prevent false signals of photoluminescence arising from non-specific binding of quantum dot secondary antibodies to the bare nickel surface, a sufficient amount of chimeric nanoparticles were added to the washed surface of the nickel nanohair as shown in the result of control of FIG. 6 (FIG. 13). Furthermore, Troponin I in A141 patient sera was successfully detected using the same assay system and procedure, while the Troponin I-free PBS buffer and healthy sera gave only negligible signals (FIG. 6).

One of the distinct advantages of this assay system according to the present invention is that one nickel nanohair structure can be repeatedly used for multiple samples. Through washing and rinsing (i.e., in the step A of FIG. 7), the used nickel nanohair was refreshed and reused for another sample assay. All of the three separate nickel nanohair structures were successfully used for the consecutive assay of eight different samples. Each consecutive assay showed reproducible and consistent signals for all the samples tested.

Figure 9:
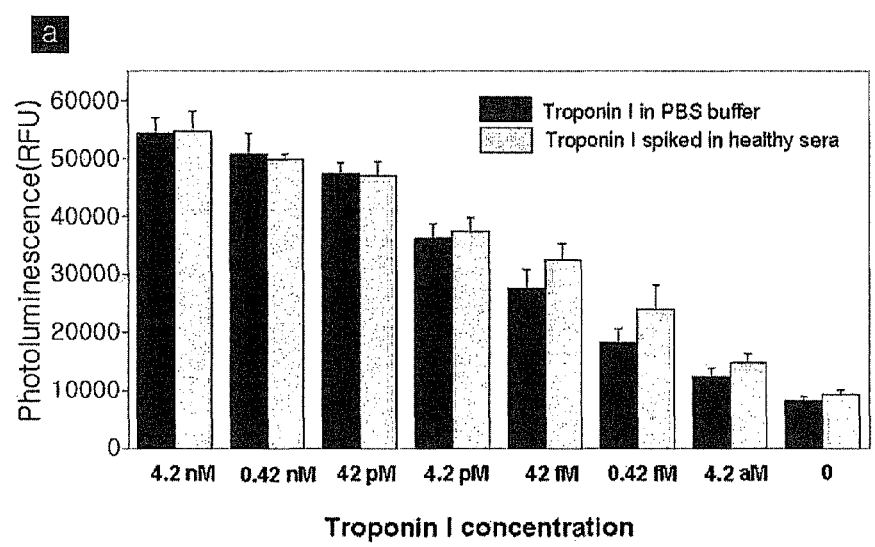
FIGS. 9 and 10 show Troponin I assay on PVDF membranes.
Figure 10:
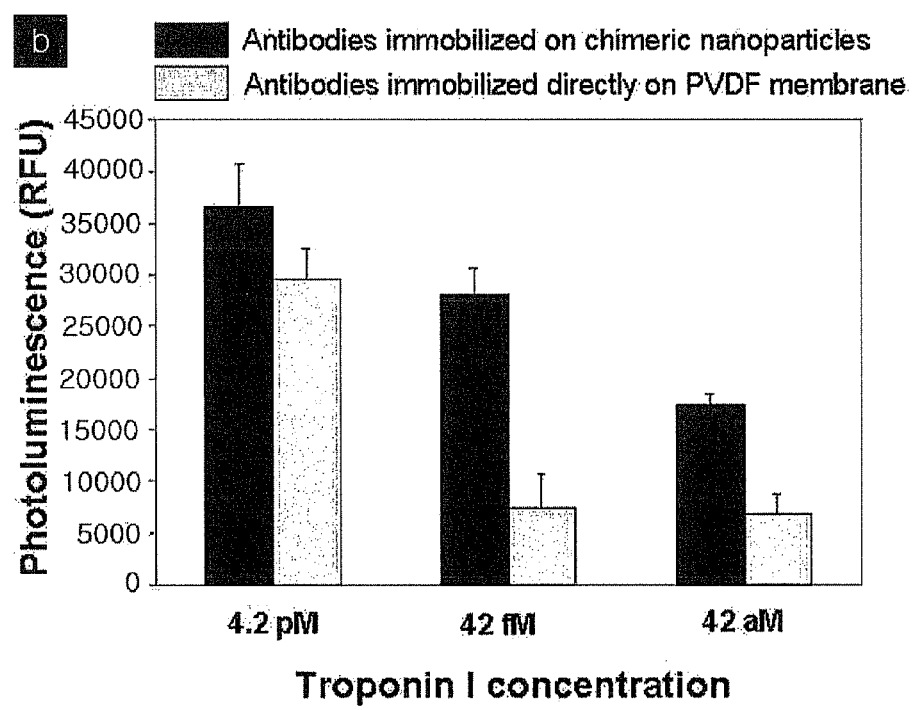

A polyvinylidene fluoride (PVDF) membrane with an average pore size of 450 nm was selected as a suitable nanostructure with a hydrophobic pore surface on which the chimeric nanoparticles were easily immobilized, and was used to construct another type of three-dimensional assay system. As seen in FIG. 9, antibodies attached on the chimeric nanoparticles could reproducibly detect Troponin I, at all concentrations, in both PBS buffer and healthy sera spiked with Troponin I. The attomolar detection limit of Troponin I was also comparable to that of the nickel nanohair-based assay. Furthermore, the assay with antibodies directly immobilized on the PVDF surface showed significantly lower sensitivities than assays using the chimeric nanoparticles (FIG. 10). This is probably due to the orientation of the antibodies; those immobilized directly on the PVDF surface may be random and have lower accessibility to Troponin I. The orientation of antibodies immobilized on the chimeric nanoparticles seems crucial for the sensitivity of the assay.

Figure 11:
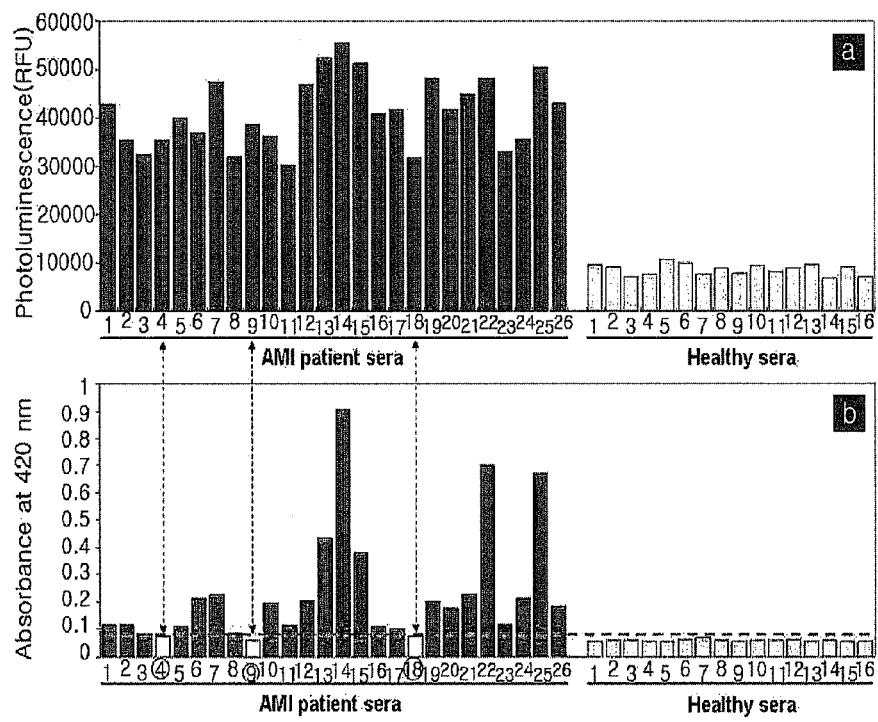
FIGS. 11 and 12 show clinical specificity and sensitivity of the viral chimeric nanoparticle-based assay. In assays of sera derived from 16 healthy individuals and 26 AMI patients, using the chimeric nanoparticles and PVDF membrane system [see FIG. 11(a)] unambiguously detected Troponin I in all patients, but using an ELISA-based diagnosis [see FIG. 11(b)] failed to detect three patients (Nos. 4, 9, and 18) and revealed nine ambiguous signals close to the clinical cutoff signal (horizontal dotted line).
Figure 12:
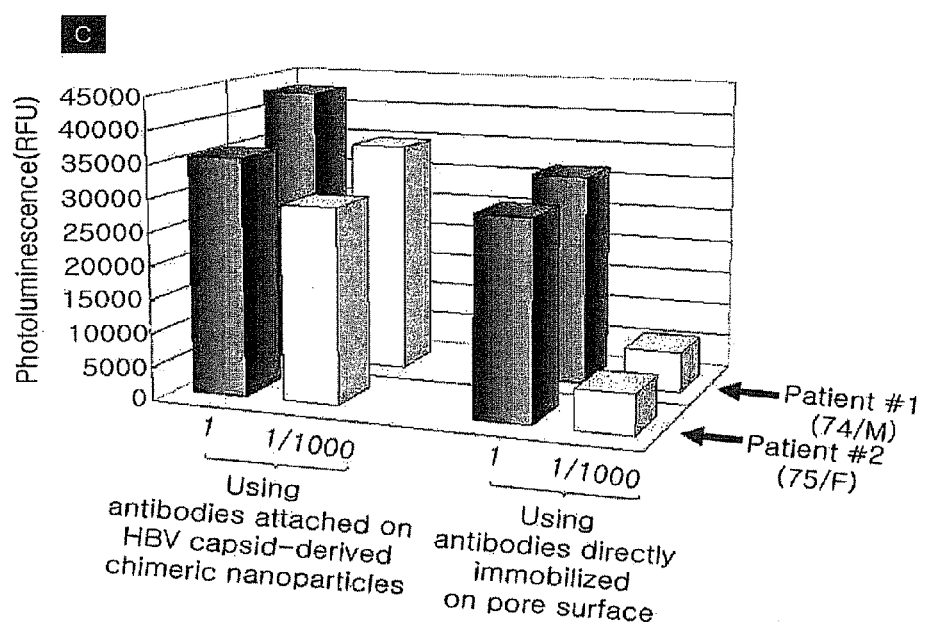

The present inventors also tested the PVDF-based assay system in the clinical diagnosis of 26 AMI patients (Table 1) who were confirmed to have experienced an AMI, and the assay results were compared with the ELISA-based assay (*a* and *b* of FIG. 11). In the ELISA-based assay (*b* of FIG. 11), three (Nos. 4, 9, and 18) AMI patient sera were not positively detected; that is, the absorbance signals were below the clinical cutoff value (indicated by the horizontal dotted line), and the signals from nine (Nos. 1, 2, 3, 5, 8, 11, 16, 17, and 23) AMI patient sera were positive but very close to the clinical cutoff. Meanwhile, the chimeric nanoparticles and PVDF-based assay gave clear positive signals for all 26 AMI patient sera, therefore indicating 100% clinical specificity (FIG. 11). (The ELISA assay results were not surprising because the clinical specificity of the ELISA kit is reported by the supplier to be 87.5%) Furthermore, antibodies directly immobilized on the PVDF surface failed to diagnose the 1,000-times diluted AMI patient sera, whereas the chimeric nanoparticles and PVDF-based assay could detect Troponin I in the diluted patient sera (FIG. 12), indicating that this three-dimensional assay can discriminate the onset of AMI even with an extremely small quantity of patient sera.

Using the HBV capsid-derived chimeric nanoparticles and three-dimensional nanostructures (nickel nanohair and PVDF membrane), we were able to develop a highly sensitive and specific assay system for the specific AMI marker, Troponin I. Although HBV capsid according to the present invention was used in this study as a model viral scaffold for the surface display of SPA$_B$, other viruses or virus-like particles could also be used for the production of chimeric nanoparticles, displaying the surface SPA$_B$. Owing to the controlled orientation of densely immobilized antibodies and the three-dimensional manner of protein capture, the assay sensitivity and clinical specificity were significantly enhanced as compared to the conventional ELISA assay.

In addition, hereinafter, the three-dimensional nanostructure-based nanosensor for detecting a disease marker using the nanostructured quartz according to the present invention will be disclosed.

1. Fabrication of Nanostructured Quartz

The present inventors developed a new method that can efficiently control the spacing of nanostructures. The proposed novel method consists of two simple stepwise RIE treatments: 1) $O_2$ RIE of a poly(methyl methacrylate) (PMMA) spin-coated quartz sample, which generates a dot-like polymeric pattern, and 2) $CF_4$ RIE to induce RIE grass selectively on top of the dot-like pattern and to etch the quartz where the RIE grass is absent, leading to the formation of a pillar-like structure.

Figure 14:
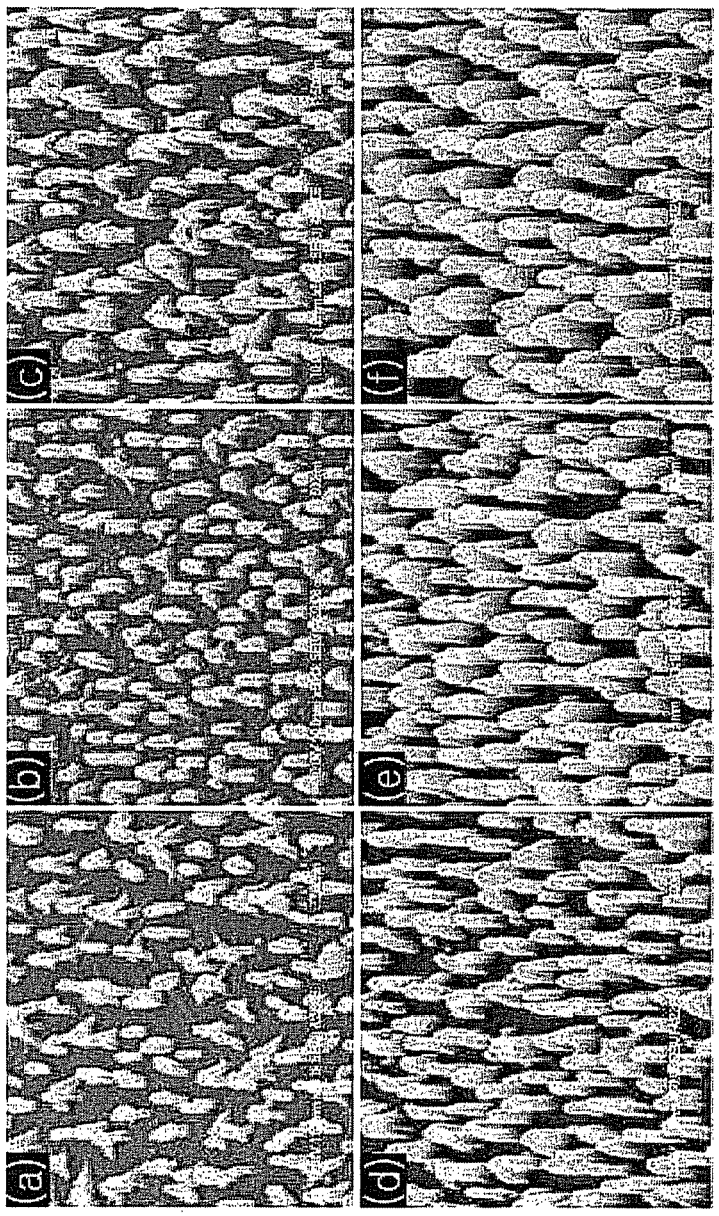
FIG. 14 shows time-dependence of dry-etching by $CF_4$ plasma. Dot patterns were formed by 1-min $O_2$ RIE and subjected to $CF_4$ RIE for a) 0 s and b) 30 s, and c) 1 min, d) 2 min, e) 3 min, and f) 4 min. SEM images were obtained using Hitachi S-4700 FE-SEM.
Figure 15:
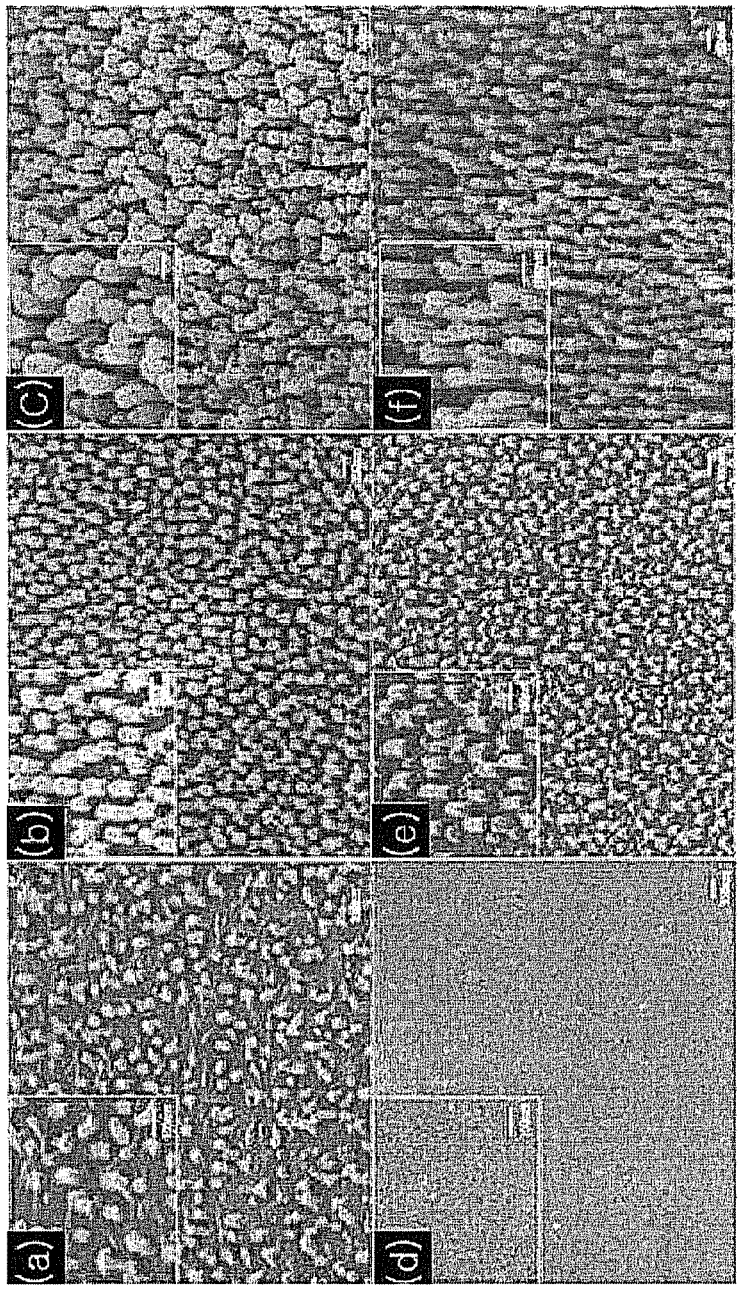
FIG. 15 shows SEM images of dry-etched dot patterns before and after the cleaning processes: a) 1 min $O_2$ RIE (without $CF_4$ RIE) and without any cleaning processes; b) 1 min $O_2$ RIE and 2 min $CF_4$ RIE followed by immersion in ethyl acetate and cleaning; c) 1 min $O_2$ RIE and 10 min $CF_4$ RIE followed by immersion in ethyl acetate and cleaning; d) 1 min $O_2$ RIE (without $CF_4$ RIE) followed by immersion in ethyl acetate and cleaning; e) 1 min $O_2$ RIE and 2 min $CF_4$ RIE followed by immersion in ethyl acetate, subsequent 1-h heating at 900° C. and cleaning; and f) 1 min $O_2$ RIE and 10 min $CF_4$ RIE followed by immersion in ethyl acetate, subsequent 1-h heating at 900° C. and cleaning. SEM images were obtained using JEOL JSM-6701F field-emission (FE)-SEM.
Figure 20:
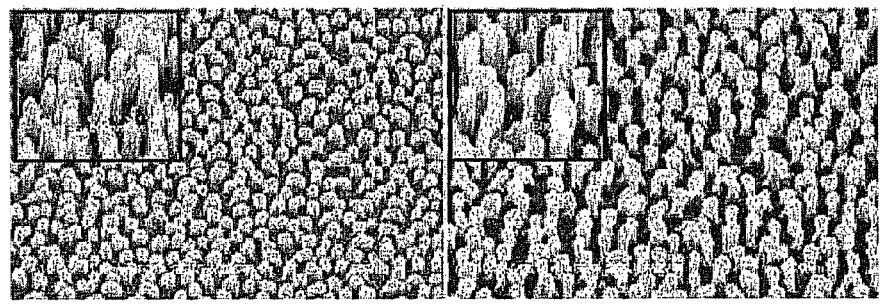
FIG. 20 shows SEM image of self-masking dot pattern formed after $O_2$ plasma exposing time of a) 15 s, b) 30 s, c) 1 min, and d) 3 min.
Figure 20:
Figure 21:
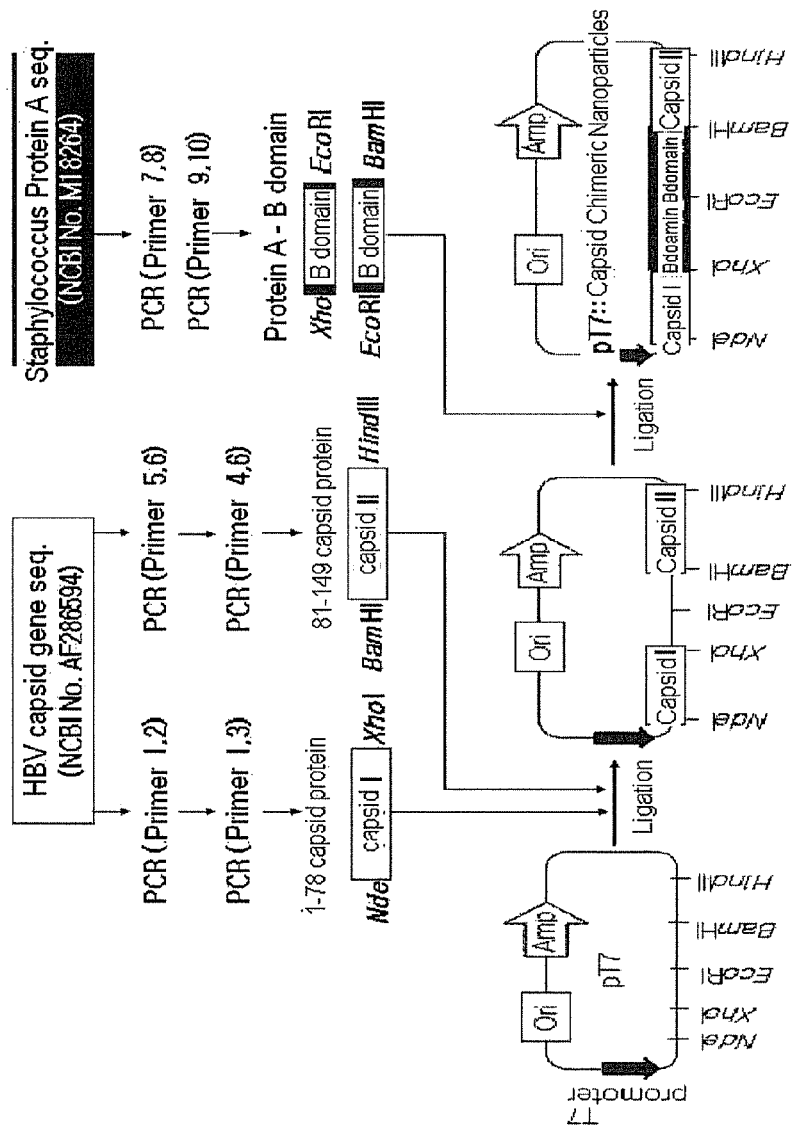
FIG. 21 shows the cleavage map and the process for fabricating an expression vector that can synthesize HBV capsid-derived chimeric nanoparticles.

FIG. 14 (*a*) shows scanning electron microscopy (SEM) images of the dot-like nanostructures formed after $O_2$ RIE of a PMMA spin-coated quartz wafer for 1 min. The spacing of the dot-like nanostructures increased according to $O_2$ RIE time. (SEM image of the spacing-controlled dot pattern formed after various $O_2$ RIE can be shown in FIG. 20 and Reference Example 1.) When the structures produced by $O_2$ RIE were subjected to 5 min of $CF_4$ RIE, pillar-like nanostructures possessing the same spacing but wider diameter were formed (see FIG. 20). FIG. 14 (*b*)~(*f*) shows that as the $CF_4$ RIE time was increased from 30 seconds to 4 minutes, the diameter and aspect ratio of the pillar-like nanostructures increased while the spacing between nanostructures remained unchanged. As the spacing and aspect ratio of the pillar-like nanostructure were dependent on $O_2$ and $CF_4$ RIE time, respectively, 1 min of $O_2$ RIE and 10 min of $CF_4$ RIE, which appeared to be suitable for biosensor applications, were chosen. X-ray photoelectron spectroscopy (XPS) analysis was performed on the sample at each step of the fabrication process (Table 3). The oxygen and silicon contents increased after 1 min of $O_2$ RIE, but the carbon content was still significantly high (33.63%) compared to the control sample (bare quartz, 7.06%), consistent with residual PMMA remaining as dot-like patterns (S3) after the $O_2$ plasma had etched the spin-coated PMMA polymer (S2). Subsequent $CF_4$ RIE induced a dramatic increase in the fluorine content (30.33%, S4) and a slight increase in the carbon content (37.83%, S4). After 13 h of soaking in ethyl acetate, the fluorine and carbon levels decreased slightly, but still remained high. The samples were soaked in ethyl acetate, a good solvent for PMMA resin, to remove any residual soluble polymer; however, it was not effective for removing the organic layer bound to the quartz surface (S5). After the soaking in ethyl acetate and drying, the outermost organic layer was successfully removed by subsequent heating at 900° C. for 1 h followed by a series of cleaning processes (cleaning with piranha solution, washing with deionized (DI) water, and blowing with nitrogen gas). After this process, the elemental composition returned to almost the same as that of the control quartz substrate (S6). FIG. 15 shows the nanostructures of the samples before and after the series of cleaning procedures including heating at 900° C. FIGS. 15(a) and (d) show that the quartz nanostructure is not formed prior to $CF_4$ RIE. FIGS. 15(e) and (f) show that the aspect ratio increases in nanopillars from 2.6±0.4 for the 2-min $CF_4$-RIE sample to 5.6±0.6 for the 10-min $CF_4$-RIE sample. From the SEM images and XPS analysis, the following mechanism can be proposed for the formation of high-aspect-ratio nanostructures: 1) $O_2$ RIE of PMMA resin produces a nanometer-scale PMMA dot-pattern on the quartz surface; and 2) the dot-like nanostructures serve as seeds for the deposition and growth of $C_xF_y$ polymer during $CF_4$ IRE and function as self-masks resistant to the chemical dry-etching. Comparison of the SEM images before and after $CF_4$ RIE discloses that the interval of the dot-like patterns is similar to that of the pillar-like structure, and the compositional changes observed in the XPS analysis support this. Additional experimental evidence supporting the proposed mechanism is provided by the removal of organic layers [FIG. 15(b), (c), (e), and (f)]. The upper area of the nanostructures differed depending on the cleaning procedures applied: less rounded and thinner structures are observed on the upper area of nanostructures in samples that were cleaned with EA followed by a series of cleaning procedures [FIG. 15(e) and (f)] in comparison with the samples cleaned with EA alone [FIGS. 15(b) and (c)]. This result indicates that the self-masking organic layer on the top of the patterns is not a soluble material, i.e., PMMA, but an insoluble material, i.e., $C_xF_y$. This 3D nanostructure has a much higher surface-to-volume ratio (about 6.0 times higher for 10 min $CF_4$ RIE sample) compared to the 2D planar quartz surface, which provides a very useful feature for highly sensitive bioassay, as demonstrated below in the present invention.

Figure 16:
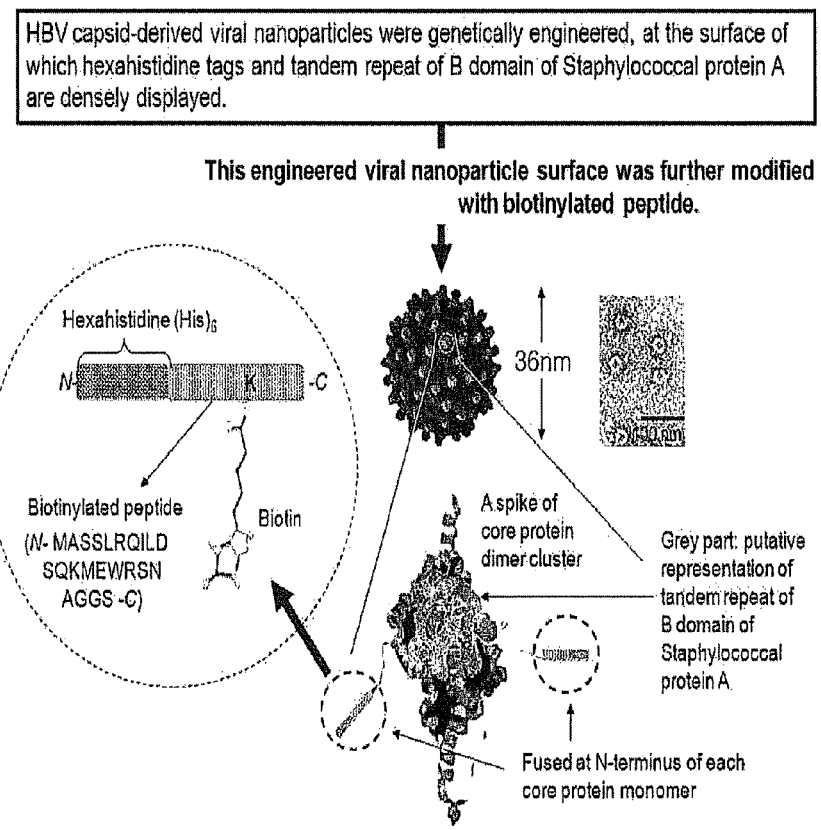
FIGS. 16 and 17 show 3D assay system based on nanostructured quartz combined with viral nanoparticles.
Figure 17:
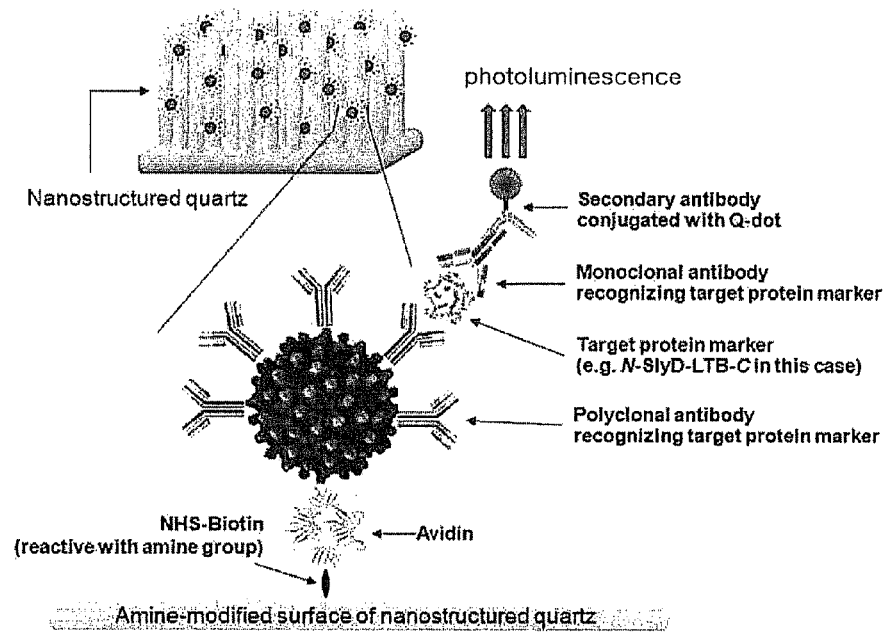

2. Sensitive Detection of Disease Markers Using Nanostructured Quartz Combined with Viral Nanoparticles In the present invention, the present inventors used the HBV capsid-derived and biotinylated nanoparticles (see Preparing Example) that are interacted with avidin molecules on the surface of nanostructured quartz (FIGS. 16 and 17). Owing to the surface-displayed $[SPA_B]_2$ of the viral particles, the nanostructured quartz surface is densely covered by probe antibodies [i.e., goat anti-LT-B immunoglobin G (IgG)] with controlled orientation, leading to the preparation of a 3D assay system (FIG. 17). As explained in FIG. 17, assay signal is photoluminescence (fluorescence) emitted from quantum dots (Q-dots) conjugated with secondary antibodies that bind specifically to mouse anti-LT-B monoclonal antibodies.

Figure 18:
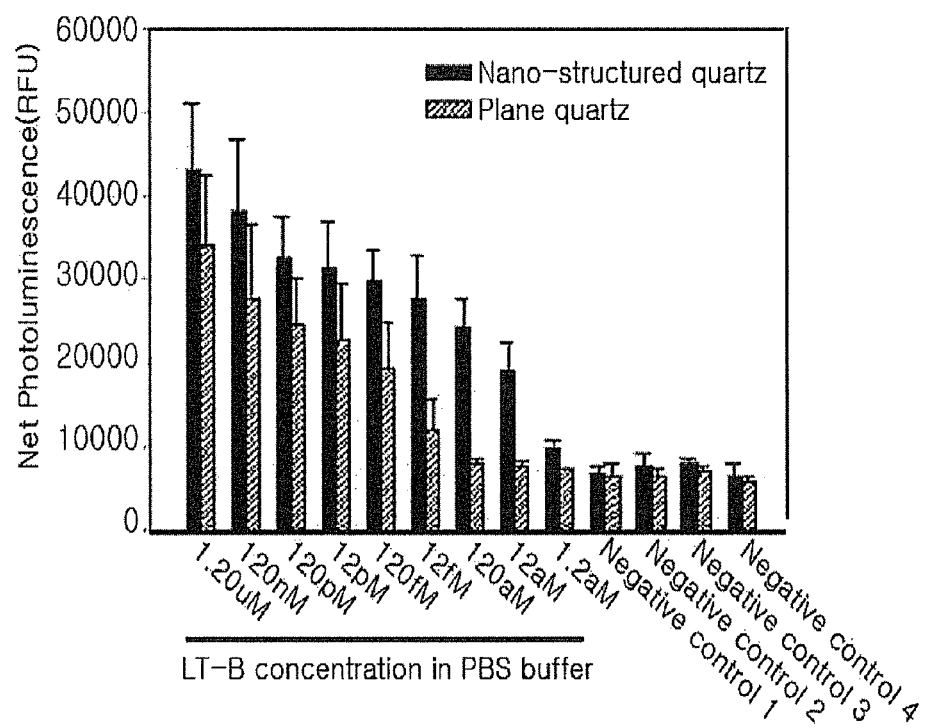
FIGS. 18 and 19 show the performance of 3D assay system.

The present inventors tried to detect LT-B at a wide range of concentrations (1.2 aM to 1.2 µM) (FIG. 18). The assay sensitivity of the nanostructured quartz-based system was also compared with that of the assay system using plane quartz. With the assay system based on the nanostructured quartz, the detection limit decreased to 12 aM of LT-B, while the plane quartz-based system was not able to detect LT-B when its concentration is lower than 1.2 fM.

According to the IUPAC (International Union of Pure and Applied Chemistry) definition, the detection limits of plane- and nanostructured quartz-based assay systems were determined to be 12 fM and 12 aM, respectively (see Reference Example 2), indicating the much higher sensitivity of nanostructured quartz.

The sensitivity of an immunoassay is directly influenced by the following three important factors: 1) density and 2) orientation of immobilized probe antibodies, and 3) accessibility of analyte antigens to the probe antibodies. It seems that the nanostructured quartz with a greater ratio of surface area to volume allows the immobilization of a greater amount of the engineered viral particles and probe antibodies. In addition to the increased surface density of probe antibodies, the orientation of immobilized antibodies was well controlled by using the surface-engineered viral particles that have selective affinity for the Fc domain of antibodies. Also, the 3D nanostructure of quartz provides the LT-B protein markers with significantly enhanced accessibility to immobilized antibodies. That is, the nanostructured quartz allows the radial diffusion of large analyte molecules, such as LT-B, and hence the increased accessibility to the sensing moieties (i.e., immobilized antibodies), while only linear diffusion happens in 2D assays using planar quartz or conventional enzyme-linked immunosorbent assay (ELISA).

As shown in FIG. 18, the nonlinearity of the fluorescent signal seems to result from self-quenching that is a general phenomenon of through-space interaction between quantum dots, which occurs when the distribution of quantum dots is unevenly polarized with high local density. In the assay system developed in the present invention, the probe antibodies are attached to the surface of viral particle via specific interactions between the antibody's Fc domain and the protein A sequences on the viral particle surface. Many antibodies (theoretically up to about 20 antibody molecules) are attached to a single viral particle with a diameter of 36 nm, and accordingly many quantum dots are subjected to being densely localized around the viral nanoparticle, which is already immobilized on the solid surface of nanostructured quartz. Reportedly, the quantum yield of quantum dots significantly diminishes when going from solution to the solid state due to the phenomenon of self-quenching (H. Skaff, K. Sill, T. Emrick, *J. Am. Chem. Soc.* 2004, 126, 11322). The self-quenching-induced decrease in fluorescent emission is also observed even when the quantum dots are present at high density in solutions (D. M. Willard, L. L. Carillo, J. Jung, A. V. Orden, *Nano Lett.* 2001, 1, 469). Similarly, it was reported that with probe antibodies labeled with multiple fluorophores, the fluorescent signal increases in a nonlinear manner with increasing number of fluorophores attached to the antobody (J. R. Lakowicz, J. Malicka, S. D. Auria, I. Gryczynski, *Anal. Biochem.* 2003, 320, 13).

Figure 19:
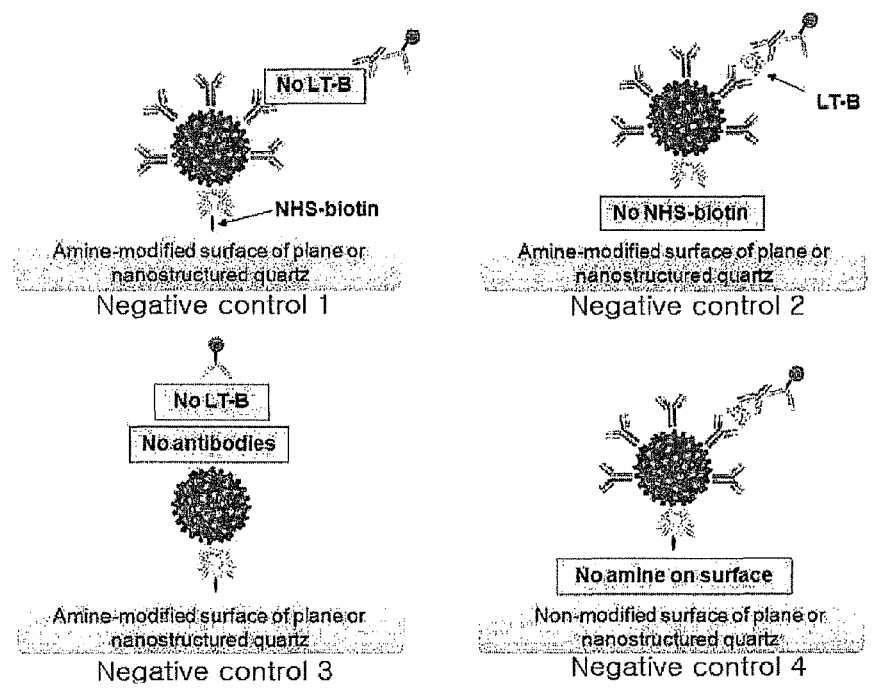

Important control experiments were also performed as shown in FIG. 19. Both of negative control 1 and 3 experiments yielded very low signals of photoluminescence (FIG. 18), indicating that without LT-B, nonspecific interactions between the two anti-LT-B antibodies (FIG. 19) are negligible and also that false signals due to nonspecific binding of Q-dot-conjugated secondary antibodies do not occur. No biotinylation and no amination of the quartz surface (i.e., the negative control experiments 2 and 4 of FIG. 19) also resulted in negligible fluorescent signals (FIG. 18). Consequently, the results in FIGS. 18-19 show that using the assay system and procedures used in the present invention, reliable and sensitive assays can be achieved without any nonspecific false signals.

The nanohair wire structure, according to the present invention, can be used for the chemical detection, which requires a high yield and efficiency, because it can exclude the agglomeration phenomenon among the nanowires. And also, it has a high applicability in the flied of biotechnology (BT) as well as nanotechnology (NT) by synthesizing the nanowire material inside the nanotemplate with a biological functionality. The present invention showed that the assay system according to the present invention using chimeric nanoparticles and three-dimensional nanostructure (nickel nanohair and PVDF membrane) has a very high sensitivity and specificity as the use of detecting the disease diagnosis marker and has very high sensitivity and specificity to the protein marker, such as Troponin I or specific AMI marker.

In addition, the proposed method to prepare high-aspect-ratio pillar-like nanostructures over a large area of a quartz surface is based on a simple and cost-effective technology that does not require expensive masking procedures to control the dimensional features of the pattern. Thus, the method can be widely used for the mass-production of size-controlled nanopatterns for advanced research and further applications. As an example, the present inventors developed a highly sensitive biosensor to detect the E. coli enterotoxin marker. By combining the engineered viral particles derived from HBV capsid with the nanostructured quartz, the present inventors constructed a novel 3D assay system and successfully detected the target enterotoxin marker even at attomolar concentrations, suggesting that sensitive diagnosis may be possible at very early stages of ETEC infection. The assay system according to the present invention has important advantages over other assay methods, such as ELISA. It solves the general assay problem, that is, dense immobilization of probe antibodies is possible on 3D surfaces by solving the random orientation problem of antibodies. More importantly, the nanostructured quartz provides the target marker with significantly enhanced accessibility to probe antibodies. Also, this assay system does not require chemical modification of probe antibodies that may significantly reduce antigen-binding ability of antibodies due to undesirable modification of active sites. Furthermore, the antibody immobilization method using the biotinylated viral particles can be applied to any assay systems employing amine-exposed surface. Although the bacterial enterotoxin was assayed here for proof-of-concept, this approach should be applicable to the detection of almost all protein disease markers, and hence has a great potential for use in sensitive and early detection of various disease markers.

EXAMPLES

The present invention will now be described in more detail with reference to the following non-limited Examples. However, the following Examples are only for illustration to explain the present invention, but the range of the present invention will not be limited to the following Examples.

Example 1

Method for Synthesizing Nickel Nanohair Structure

—Synthesize of Nickel Nanowires—

The anodized aluminum oxide (AAO) nanotemplate with uniform pore diameter (dozens nm~hundreds nm) as shown in FIG. 1(a) was synthesized. And then, Ag as a working electrode was deposited one side of AAO in a thickness of 250~350 nm using E-beam evaporator as shown in FIG. 1(b). Then, after adding AAO to the solution of Nickel Sulfate ($NiSO_4.6H_2O$, 0.5M)+Nickel Chloride ($NiCl_2.6H_2O$, 0.1M)+Boric acid ($H_3BO_3$, 0.1M) as shown in FIG. 1(c), Pt as a counter electrode was deposited to the nickel nanowires. Here, nickel sulfate is a main component of plating; nickel chloride was used for increasing an electrical conductivity; and boric acid was used as a buffer solution for pH homeostasis.

—Planarization of Nickel Nanowires—

Then, as shown in FIG. 1(c), the polishing was performed about 10 μm through a chemical mechanical polishing (CMP) process for identifying AAO nanotemplate with the height of nanowires that were overflow or underflow-grown inside the AAO.

—Exposure of Nickel Nanowires on AAO—

As a final step, a selective reactive ion etching (RIE) process of AAO nanotemplate was performed in order to expose the nickel nanowires. The process was performed by etching AAO for 10 min at an etching rate of 0.25 μm/min using $BCl_3$ (100%) gas. And then, a cleaning process (DI water: ultrapure water, ethanol) was completed, finishing the process of the nickel nanohairs structure with a clean surface.

Example 2

Biosynthesis of HBV Capsid-Derived Chimeric Nanoparticles

Following assembly PCR using the primers as disclosed in the following Table 1, the present inventors prepared the two gene clones derived from the HBV core protein (HBVcAg) gene and code for the synthesises of N-NdeI-hexahistidine-HBVcAg(1-78)-G4SG4T-XhoI-C and N-BamHI-G4SG4-HBVcAg(81-149)-HindIII-C. To replace the P79A80 of the HBV cAg with the tandem repeat of $SPA_B$ (residues 209-271), the two different clones, N-XhoI-$SPA_B$-EcoRI-C and N-EcoRI-$SPA_B$-BamHI-C were prepared. Through the sequential ligation of the four above gene clones into plasmid pT7-7, we constructed the plasmid expression vector pT7-Chimera-HBV encoding the synthesis of N-$His_6$-HBVcAg (1-78)-$SPA_B$-$SPA_B$-HBVcAg(81-149)-C. After the complete DNA sequencing of gel-purified plasmid expression vector, E. coli strain BL21 (DE3) [F$^-$ompThsd$S_B$(rB$^-$mB$^-$)] was transformed with pT7-Chimera-HBV, and ampicillin-resistant transformants were selected. The gene expression, purification and TEM image analysis of chimeric nanoparticles were performed by using the same method as disclosed in Ahn, J. Y. et al. *Nucl. Acids Res.* 3751-3762 (2005).

The information and the disclosure in more detail about the primer sequences and templates related to the fabrication of HBV capsid-derived chimeric nanoparticles are as follows:

TABLE 1

| Gene Name | | Primer | Seq. No. | Sequence |
|---|---|---|---|---|
| Hepatitis B virus capsid | N-terminus of HBV capsid (1-234 Gene Sequence) | Sense | Seq. No. 1 | cat agt *cat cac cat cac cat cac* gac att gac ccg tat aaa gaa |
| | | Anti-Sense | Seq. No. 2 | <u>ccc act ccc tcc gcc acc</u> gtc ttc caa att act tcc cac cca |
| | | Anti-Sense | Seq. No. 3 | ctc gag <u>agt acc gcc tcc ccc act ccc tcc gcc acc</u> |
| | C-terminus of HBV capsid (241-447 Gene Sequence) | Sense | Seq. No. 4 | gga tcc <u>gga tcc ggt ggc gga ggg tct ggg gga ggc ggt</u> |
| | | Sense | Seq. No. 5 | <u>ggc gga ggg tct ggg gga ggc ggt</u> tcc agg gaa tta gta gtc agc tat |
| | | Anti-Sense | Seq. No. 6 | aag ctt tta aac aac agt agt ttc cgg aag |
| B domain of *Staphylococcal* protein A | | Sense | Seq. No. 7 | ctc gag gca ccg aaa gct gat aac |
| | | Anti-Sense | Seq. No. 8 | gaa ttc gtc agc ttt tgg tgc ttg |
| | | Sense | Seq. No. 9 | gaa ttc gca ccg aaa gct gat aac |
| | | Anti-Sense | Seq. No. 10 | gga tcc gtc agc ttt tgg tgc ttg |

Table 1 shows primer sequences, in which bold types represent restriction enzymes sequences; underlined parts represent linker sequences; and italic types represent 6 histidine sequences.

HBV capsid-derived chimeric nanoparticles can be largely divided into 1-78 amino acid sequence regions of capsid protein, the region including continuously two Staphylococcal protein A, and 81-149 amino acid sequences regions of capsid protein (1-78 sequences of capsid protein is NCBI Nucleotide accession number: AF286594 sequences: 1901-2134 (Sequence No. 12) and amino acid sequence (Sequence No. 13); 81-149 sequences of capsid protein is 2141-2347 sequences (Sequence No. 14) of AF286594; and the amino acid sequence is Sequence No. 15, and Protein A sequence is NCBI nucleotide accession No. M18264, nucleotide sequence 625-813 (Sequence No. 11); and the amino acid is Sequence No. 16).

The first region was subjected to extension PCR using the primer sequence region 1 including 6 histidines using the gene sequence of HBV capsid protein (1901-2452 sequences of NCBI Nucleotide accession number: AF286594 sequences) as a template, and the primer sequences 2 and 3 including a linker sequence (amino sequences GGGGSGGGGT). Firstly, after performing PCR using the primer sequences 1 and 2, PCR was performed by using the primer sequences 1 and 3 using the synthesized PCR products as the templates. As the results, PCR product consisting of 5'-NdeI-HBV capsid protein (1-78 amino acid sequences)-linker sequence (GGGGSGGGGT)-XhoI-3' was obtained.

Using the second region, two B domains of protein A forming 5'-XhoI-$SPA_B$-EcoRI-3' and 5'-EcoRI-$SPA_B$-BamHI-3' using the primer sequences 7 and 8, and 9 and 10 through using B domain part of Protein A (SPA) sequence (NCBI Nucleotide accession number: M18264) of *Staphylococcus aureus* ($SPA_B$) were obtained as PCR products.

The third region was subjected to extension PCR using the primer sequence 6, and the primer sequences 4 and 5 including the linker sequence (Amino acid sequence GGGGSGGGG) through using HBV capsid protein gene sequence as a template. Firstly, after performing PCR using the primer sequences 5 and 6, PCR was performed by using the primer sequences 4 and 6 through using the synthesized PCR products as a template. As the results, PCR product consisting of 5'-BamHI-linker sequence (GGGGSGGGG)-HBV capsid protein (81-149 amino acid sequence)-HindIII-3' was obtained.

Four PCR products produced as mentioned above were successively inserted into pT7-7 vector to construct the expression vector that can synthesize HBV capsid-derived chimeric nanoparticles (FIG. 21)

Example 3

Construction of the Three-Dimensional Diagnostic Systems Using Virus Nanoparticles Nickel Nanohair-Based System:

the nickel nanohair structure prepared by the above Example 1 was placed in the Costar 96-well plate (Cat. No. 3599, Corning, N.Y., USA). Before immobilizing the chimeric nanoparticles, the nickel nanohair in each well was washed four times for 15 min using 0.3 M sulphuric acid and then six times for 10 min using distilled water, then completely dried. Next, the background photoluminescence from the nickel nanohair structure was measured using a microplate reader (GENios, Tecan, Austria) with excitation and emission at 420 and 650 nm, respectively. PBS buffer (50 μl) containing the 38-nM chimeric nanoparticles prepared from Example 2 was added to the nickel nanohair structure, followed by slow agitation for 30 mm, after which it was washed with 50 mM Tris buffer (pH 7.4). Rabbit anti-troponin polyclonal antibody (5 μg/ml, Cat. No. ab470003, Abcam, Cambridge, UK) in 200 μl PBS buffer was added to the chimeric nanoparticles that were already immobilized on the nickel nanohair, by slowly stirring the nickel nanohair in the antibody-containing PBS buffer for 2 h.

PVDF-Based System:

PVDF membrane (Immobilion-FL, IPFL 10100, Millipore, MA, U.S.A.) in a Costar 96-well plate was pre-wetted with methanol for 1 min and washed with a PBS buffer (137 mM NaCl, 2.7 mM KCl, 10 mM $Na_2HPO_4$, 2 mM $KH_2PO_4$, pH 7.4) for 5-10 min. Before the PVDF membrane was completely dried, 10 μl of PBS buffer containing the chimeric nanoparticles purified in Example 2 was dropped onto a designated spot on the membrane. The membrane was then slowly stirred for 1 h in the blocking solution (1% skim milk) and washed twice with the PBS buffer for 30 min. Goat anti-Troponin I polyclonal antibodies (20 μg/ml in PBS buffer; Cat. No. 70-XG82, Fitzgerald, MA, USA) was added to the chimeric protein nanoparticles that were already immobilized onto the PVDF membrane, by slowly stirring the membrane in the antibody-containing 200 μl PBS buffer for 2 h.

Experimental Example 1

Detection of Troponin I and Diagnosis of AMI Patients

To the three-dimensional diagnostic system consisting of anti-Troponin I antibodies, HBV capsid-derived chimeric nanoparticles prepared in Example 2, and nickel nanohair structure (or PVDF membrane) prepared in Example 1, 200 μl Troponin (human cardiac Troponin I-T-C complex, Cat. No. 8T62, HyTest, Finland) that had been properly diluted in PBS buffer or human serum (AMI patient or healthy serum) was added, then stirred for 20 s, and incubated at room temperature for 1 h. After washing for 5 min using PBS buffer, 200 μl mouse anti-Troponin I monoclonal antibodies (3.2 μg/ml, Cat. No. 4T21, HyTest, Finland) in PBS buffer was added, stirred for 20 s, incubated at room temperature for 1 h, and then washed for 5 min using PBS buffer. 200 μl Q-dot (CdSe)-secondary Ab conjugate [1 nM, Qdot 655-Goat F(ab')2 anti-mouse IgG conjugate, Cat. No. Q11021MP, Invitrogen, Carlsbad, Calif., USA] was added, stirred for 20 s, incubated at room temperature for 1 h, and finally washed for 10 min with PBS buffer. Photoluminescence was then measured using a microplate reader (GENios, Tecan, Austria) with excitation and emission at 420 and 650 nm, respectively.

All the ELISA assay experiments in the present invention were conducted using the commercial ELISA Troponin assay kit (Troponin I EIA, Cat. No. 25-TR1HU-E01, 96 wells, ALPCO Diagnostics, NH, USA) that was developed for in vitro diagnostic use. In short, it is as follows: 1) 100 μl of human serum (AMI patient or healthy serum) or Troponin (human cardiac Troponin I-T-C complex, Cat. No. 8T62, HyTest, Finland) in PBS buffer was added to antibody-coated 96-wells microplate provided by a provider; 2) 100 μl of enzyme conjugated reagent (containing HRP enzyme-conjugated anti-Troponin I antibodies) was added to each well, stirred sufficiently for 30 s, incubated at room temperature for 90 min, and then washed five times with distilled water; 3) after the well was allowed to strike hard it on an absorption paper in order to remove the entire remained water drop, 100 μl of "TMB reagent (containing the substrate to HRP enzyme)" was added to each well, mixed for 5 s, and then incubated at room temperature for 20 min; 4) 100 μl of "Stop solution" was added to each well in order to stop the enzyme reaction, then mixed for 30 s, and then the absorbance was measured by using the microplate reader (GENios, Tecan, Austria) at 420 nm.

Troponin I EIA provides a reliable assay for the quantitative measurement of human cardiac-specific Troponin I with a clinical specificity of 87.5%. The procedure disclosed in Troponin I EIA protocol was strictly followed for the Troponin I assay, and the assay procedure is as follows. The entire list of AMI patients and healthy sera are disclosed in Table 2.

TABLE 2

| No. | Age | Sex | Hospital |
|---|---|---|---|
| AMI Patient Serum | | | |
| 1 | 74 | M | KangNam Sacred Heart Hospital |
| 2 | 75 | F | |
| 3 | 58 | M | |
| 4 | 68 | M | |
| 5 | 63 | M | |
| 6 | 80 | M | |
| 7 | 59 | M | |
| 8 | 68 | M | |
| 9 | 74 | M | |
| 10 | 77 | F | |
| 11 | 86 | F | |
| 12 | 85 | F | |
| 13 | 52 | F | |
| 14 | 43 | M | |
| 15 | 68 | M | |
| 16 | 59 | F | |
| 17 | 84 | F | |
| 18 | 58 | M | |
| 19 | 37 | M | |
| 20 | 42 | M | Korea University Medical Center [*: Person experienced with a myocardium damage due to a heart septal defect operation using an extracorporeal circulation] |
| 21* | 3 | F | |
| 22 | 91 | M | |
| 23 | 72 | F | |
| 24 | 79 | F | |
| 25 | 89 | F | |
| 26 | 57 | M | |
| Healthy serum | | | |
| 1 | 34 | M | Korea University Medical Center |
| 2 | 24 | M | |
| 3 | 28 | M | |
| 4 | 25 | F | |
| 5 | 45 | M | |
| 6 | 24 | M | |
| 7 | 27 | M | |
| 8 | 24 | F | |
| 9 | 31 | F | |
| 10 | 25 | M | |
| 11 | 30 | F | |
| 12 | 24 | M | |
| 13 | 26 | F | |
| 14 | 48 | M | |
| 15 | 26 | F | |
| 16 | 29 | M | |

Example 4

Preparation of Nanostructured Quartz

In order to prepare the nanostructured quartz according to the present invention, quartz wafers (Buysemi, Seoul, Korea) were first cleaned with piranha solution (7:3 v/v concentrated sulfuric acid: 35% hydrogen peroxide), rinsed with DI water, dried at 100° C. for 5 min and cooled to room temperature. Then polymeric resin, either PMMA [poly(methyl methacrylate)] A2, A8, A9 or A11 (Microchem, USA), was spin-coated onto the quartz surface at 4000 rpm for 25 s, and the wafers were postbaked at 170° C. for 30 min. $O_2$ and $CF_4$ RIE were carried out using a custom-made RIE system at 250 W, 40 mTorr, and a gas flow rate of 40 sccm. Finally, the quartz surfaces were cleaned by a series of cleaning processes. The nanostructures and atomic composition of the outermost layer were observed using FE-SEM (Hitachi S-4700, Japan) and XPS (x-ray Photoelectron Spectroscopy; PHI 5800 ESCA system, Japan), respectively. The pillar-like quartz nanostructures fabricated using this method have high-aspect-ratios and hence high surface areas.

TABLE 3

|  | C1s/% | O1s/% | F1s/% | Si2p/% |
|---|---|---|---|---|
| S1: Quartz control | 7.06 | 62.78 | 0.19 | 29.97 |
| S1: PMMA coating | 73.13 | 26.87 | 0.00 | 0.00 |
| S3: O2 1 min | 33.63 | 44.73 | 7.07 | 14.57 |
| S4: CF4 10 min | 37.82 | 24.34 | 30.33 | 7.52 |
| S5: EA soaking | 35.52 | 26.70 | 27.51 | 10.27 |
| S6: 900° C. | 9.75 | 63.04 | 0.16 | 27.05 |

The above table 3 shows the results of XPS at each successive step to the fabrication of nanostructures.

Example 5

Synthesis of HBV Capsid-Derived and Biotinylated Nanoparticles

The present inventors genetically engineered HBV capsid particles (consisting of the 240 truncated mutants of HBV core protein) [B. Bottcher, S. A. Wynne, R. A. Crowther, Nature 1997, 386, 88; R. A. Crowther, N. A. Kiselev, B. Bottcher, J. A. Berriman, G. P. Borisova, V. Ose P. Pumpens, Cell 1994, 77, 943]) by inserting the tandem repeat of the B domain of Staphylococcal protein A [$(SPA_B)_2$] into the surface loop of HBV core protein mutant, so that antibodies [immunoglobulin G (IgG)] can bind and form a dense carpet around each viral particle via specific interactions between $(SPA_B)_2$ and the Fc domain of IgG (J. S. Park, M. K. Cho, E. J. Lee, K. Y. Ahn, K. E. Lee, J. H. Jung, Y. Cho, S. S. Han, Y. K. Kim, J. Lee, Nat. Nanotechnol. 2009, 4, 259). In the present invention, the present inventors further modified the HBV capsid particles by adding special biotinylated peptides; that is, a biotinylated peptide sequence was additionally inserted between the polyhistidine tag and the N-terminus of the HBV core protein mutant. The biotinylated peptide sequence (MASSLRQILDSQKMEWRSNAGGS; Sequence No. 17) was added to the N-terminal of the HBV core protein by extension polymerase chain reaction (PCR) using appropriate primers. After the complete sequencing of the recombinant gene clone encoding the synthesis of the biotinylated HBV core protein, followed by the construction of expression vector using plasmid vector pT7-7, E. coli strain BL21 (DE3) was transformed with the expression vector, and the ampicillin-resistant transformants were finally selected (J. S. Park, M. K. Cho, E. J. Lee, K. Y. Ahn, K. E. Lee, J. H. Jung, Y. Cho, S. S. Han, Y. K. Kim, J. Lee, Nat. Nanotechnol. 2009, 4, 259; J. Y. Ahn, H. Choi, Y. H. Kim, K. Y. Han, J. S. Park, S. S. Han, J. Lee, Nucl. Acids Res. 2005, 33, 3751). To induce the recombinant gene expression, 1 mM isopropyl-β-D-thiogalactopyranoside (IPTG) was added to the culture medium containing biotin (10 µg/ml Sigma, USA). Finally, the self-assembled nanoparticle formation of the biotinylated core protein mutants was confirmed through TEM image analysis (FIG. 15).

Example 6

Construction of 3D Assay System Based on Nanostructured Quartz Combined with Viral Nanoparticles The immobilization of probe antibodies started with amination of the nanostructured quartz surface by immersion in a solution (1 mM in toluene) of 3-aminopropyldiethoxysilane (APS) (Gelest Inc, USA) for 1 h. The aminated surfaces were then biotinylated by immersing the aminated samples in the solution of biotin 3-sulfo-N-hydroxysuccinimide ester sodium salt (Sigma, USA) [2 mM in a mixture of dimethyl sulfoxide (DMSO) and phosphate buffered saline (PBS)] for 6 h. The biotinylated quartz samples were rinsed with DMSO/PBS followed by DI water and dried at room temperature. The biotin modified quartz was incubated with avidin (10 µM, Sigma, USA) in PBS for 3 h at room temperature to link avidin molecules to the surface of quartz, washed with PBS twice for 15 min, and then incubated with the biotinylated HBV capsid particles (0.5 mg/ml) for 6 h at 10° C. After immersion in 5 bovine serum albumin (BSA, Thermo scientific, USA) for 12 h at 4° C., the engineered viral particle-coated quartz surface was washed twice with PBS for 15 min, incubated with 400 µl of goat anti-LT-B-antibodies (20 µg/ml IgG in PBS buffer, Gene Tex, USA) per a well with slow stirring for 3 h, and washed twice with PBS for 15 min.

Experimental Example 2

Assay of ETEC LT-B Marker

The LT-B marker diluted in PBS buffer (500 µl) was added to the 3D assay system and stirred at room temperature for 1 h. The LT-B marker used in the present invention was a recombinant fusion protein N-SlyD-LT-B-C consisting of N-terminal fusion expression partner, and E. coli slyD (the synthesis of N-SlyD-LT-B-C is further explained in the Supporting Information). Following the repeated 10-min washing steps with LT-B-free PBS buffer, mouse anti-LT-B monoclonal antibodies (10 µg/ml IgG, Abcam, UK) in PBS (500 µl) was added, stirred at room temperature for 1 h, and washed twice for 10 min with PBS buffer. 500 µl of Qdot (CdSe)-secondary Ab conjugate (1 nM, Invitrogen, CA) was added, stirred at room temperature for 1 h, and then washed twice for 10 min with PBS buffer. Fluorescence was measured using a microplate reader (GENios, Tecan, Austria) with excitation and emission at 420 and 650 nm, respectively.

Reference Example 1

SEM images of Self-Masking Dot Patterns Formed after $O_2$ Plasma Exposure Times of (a) 15 s, (b) 30 s, (c) 1 min, and (d) 3 min The figures inserted show dry-etched patterns formed when treating $CF_4$ plasma for 5 min. SEM images were obtained by using Hitachi S-4700 FE-SEM.

Reference Example 2

Determination of Limit of Detection (LOD)

In the present invention, the present inventors determined LOD according to IUPAC definition (IUPAC Compendium of Chemical Technology, $2^{nd}$ ed., 1997). "The limit of detection" represented as the concentration or amount is derived from the smallest value, $X_L$ that can be detected with a definite decision to the given analysis process. $X_L$ value is an equation, $X_L=X_{bi}+kS_{bi}$, and here $X_{bi}$ is average of blank value, $S_{bi}$ is a standard deviation of blank value, and k is a number factor selected according to the desired reliability. According to the recent research articles (L. Soleymani, Z. Fang, E. H. Sargent, and S. O. Kelley, *Nat. Nanotechnol.* 2009, 4, 844; K. Dore, S. Dubus, H. A. Ho, I. Levesque, M. Brunette, G. Corbeil, M. Boissinot, G. Boivin, M. G. Bergeron, D. Boudreau, M. Leclerc, *J. Am. Chem. Soc.* 2004, 126, 4240; A. Hucknall, D. H. Kim, S. Rangarajan, R. T. Hill, W. M. Reichert, A. Chilkoti *Adv. Mater.* 2009, 21, 1968; S. Majd, E. C. Yusko, A. D. MacBriar, J. Yang, M. Mayer, *J. Am. Chem. Soc.* 2009, 131, 16119); k value is selected as 3.0. The present inventors determined LOD of analysis system as disclosed in the following Table. The limits of detection of plain- and nanostructured quartz-based analysis system were 12 fM and 12 aM, respectively.

TABLE 4

| LT-B Marker Con. | Plane quartz Fluorescence measure mean | Nanostructed quartz Fluorescence measure mean |
|---|---|---|
| 1.2 μM | 34317 | 43049 |
| 120 nM | 27840 | 38257 |
| 120 pM | 24651 | 32538 |
| 12 pM | 22687 | 31282 |
| 120 fM | 19479 | 29812 |
| 12 fM | 12019 | 27883 |
| 120 aM | 8052 | 24246 |
| 12 aM | 7656 | 19275 |
| 1.2 aM | 7565 | 10063 |
| Negative control 1 | 6571 | 6818 |
| Negative control 2 | 6584 | 7800 |
| Negative control 3 | 7061 | 8108 |
| Negative control 4 | 6107 | 6595 |
| Blank signal average ($X_{bi}$) | 6538 | 7248 |
| Blank signal SD average ($S_{bi}$) | 880 | 1342 |
| $X_{bi} + 3 \cdot S_{bi}$ | 9179 | 11274 |
| Limit of detection | 12 fM | 12 aM |

Reference Example 3

Biosynthesis of LT-B Marker (N-SlyD-LT-B-C)

*E. coli* heat-sensitive enterotoxin (LT) gene received from Korea Center for Disease Control and Prevention (Seoul, Korea). The present inventors amplified the gene encoding B subunit (LT-B) of LT enterotoxin by using the suitable PCR primers [Sense primer: CTCGAG GCT CCT CAG TCT ATT (Sequence No. 18), Antisense primer: AAGCTT TTA GTT TTC CAT ACT GAT (Sequence No. 19), and here the underlined parts are the restriction enzyme sequences]. In order to produce an aqueous and active type of LT-B, SlyD (i.e., *E. coli* FKBP-type peptidyl-prolyl cis-trans isomerase) gene was fused to 5'-terminal of LT-B gene with the restriction enzyme site: 5-NdeI-SlyD-XhoI-LT-B-HindIII-3'. The present inventors constructed the expression vector synthesizing N-His$_6$-SlyD-LT-B-C through the ligation of gene clone with plasmid pET28a (Novagen, Germany). After transforming with the expression vector, kanamycin-resistant transformants of *E. coli* BL21 (DE3) were selected. The recombinant *E. coli* was incubated at the shaking flask (250-mL Erlenmeyer flasks, 37° C., 200 rpm) containing 50 mL Luria-Bertani (LB) medium (contained with 100 mg L$^{-1}$ kanamycin). When the medium turbidity ($OD_{600nm}$) was reached to about 0.6-0.7, IPTG (Isopropyl-β-D-thiogalactopyranoside) (1 mM) was added to induce the expression of recombinant gene. After incubating at 20° C. for overnight, recombinant *E. coli* cells were centrifuged at 13,000 rpm for 10 min to collect the bacterial precipitation. The cell pellet was suspended to 5 ml lysis buffer (pH 8.0, 50 mM sodium phosphate, 300 mM NaCl, 20 mM imidazole) containing DNase I (Roche Diagnostics, Mannheim, Germany), and then sonicated by using Sonifer (Branson Ultrasonics Corp., Danbury, Conn., USA). The cell-free supernatant was separated by centrifuging at 7,000 rpm for 10 min, and then finally the recombinant fusion protein SlyD::LT-B was separated by using Ni$^{2+}$-NTA column (Qiagen, Hilden, Germany) (Washing Buffer: pH 8.0, 50 mM sodium phosphate, 300 mM NaCl, 80 mM imidazole/ Elution Buffer: pH 8.0, 50 mM sodium phosphate, 300 mM NaCl, 200 mM imidazole).

Example 7

Figure 22:
FIG. 22 shows a drawing an expression vector that can synthesize HBV capsid-derived chimeric fluorescent nanoparticles by successive insertion of 6 PCR products to pT7-7 vector.
Figure 22:
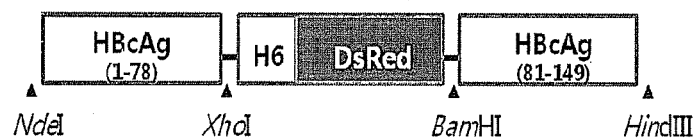
Figure 22:
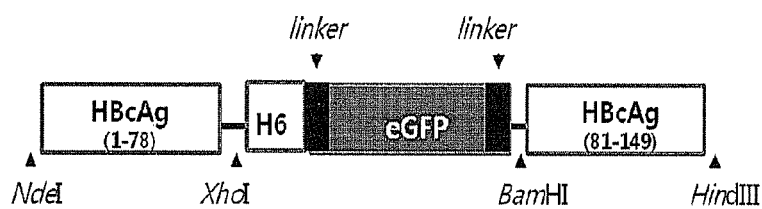
Figure 22:
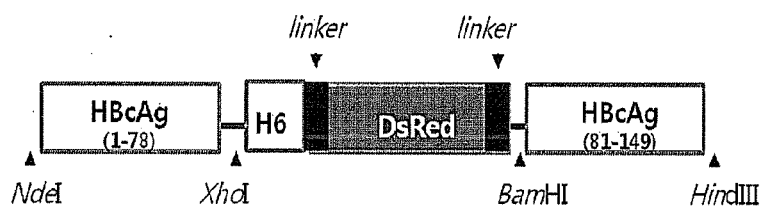

Preparation of Expression Vector for Biosynthesis of HBV Capsid-Derived Chimeric Fluorescence Nanoparticles After PCR using the primers disclosed in the following Table 5, two gene codes encoding the synthesises of N-NdeI-HBVcAg(1-78)-XhoI-C and N-BamHI-HBVcAg(81-149)-HindIII-C derived from HBV core protein (HBVcAg) gene were obtained. In addition, 5'-XhoI-hexahistidine-linker-eGFP-linker-BamHI-3' and 5'-XhoI-hexahistidine-linker-DsRed-linker-BamHI-3' inserted with 5'-XhoI-hexahistidine-EGFP-BamHI-3', 5'-XhoI-hexahistidine-DsRed-BamHI-3' and linker (G3SG3TG3SG3), i.e., four different clones were prepared by using PCR or extension PCR in order to replace a fluorescent protein (Enhanced green fluorescent protein; eGFP or red fluorescent protein; DsRed) with P79A80 of HBVcAg. Four plasmid expression vectors, i.e., pT7-fluorescence protein-HBcAg encoding the synthesises of A) N-HBVcAg(1-78)-His6-eGFP-HBVcAg(81-149)-C, B) N-HBVcAg(1-78)-His6-DsRed-HBVcAg(81-149)-C, C) N-HBVcAg(1-78)-His6-linker-eGFP-linker-HBVcAg(81-149)-C, and D) N-HBVcAg(1-78)-His6-linker-DsRed-linker-HBVcAg(81-149)-C were constructed through a sequential ligation of the gene clones to the plasmid pT7-7 (FIG. 22). The sequences of the entire plasmid expression vectors constructed were confirmed through complete DNA sequencing after gel-purification.

The information and the more detailed disclosure about the primer sequence and template related to the preparation of HBV capsid-derived chimeric nanoparticles are disclosed as follows (Table 5):

1) The first region was subjected to PCR using 1 primer sequence region including restriction enzyme NdeI and 2 primer sequence region including restriction enzyme XhoI by using the gene sequence of HBV capsid protein (NCBI Nucleotide accession number: 1901-2452 sequence of AF286594 sequences) as a template. As a result, PCR product consisting of 5'-NdeI-HBV capsid protein (1-78 Amino acid sequence)-XhoI-3' was obtained.

2) The second region was subjected to PCR using 3 primer sequence region including restriction enzyme BamHI and 4 primer sequence region including restriction enzyme HindIII by using the gene sequence of HBV capsid protein as a template. As a result, PCR product consisting of 5'-BamHI-HBV capsid protein (81-149 amino acid sequence)-HindIII-3' was obtained.

3) The third region was subjected to PCR using 5 primer sequence (or 7 primer sequence) including XhoI and hexahistidine and 6 primer sequence (or 8 primer sequence)

including BamHI by using the gene sequence of eGFP (or DsRed) as a template. 5 and primer sequences were used for preparing 5'-XhoI-His6-eGFP-BamHI-3' and 7 and 8 primer sequences were used for preparing 5'-XhoI-His6-DsRed-BamHI-3'.

4) The fourth region was subjected to PCR using 11 and 12 primer sequences (DsRed) or 9 and 10 primer sequences (eGFP) including linker sequence (amino acid G3SG3TG3SG3) by using the sequence of eGFP (or DsRed) as a template, and then was again subjected to PCR using 13 and 15 primer sequences by using PCR product synthesized as a template. Then, the secondary extension PCR was performed by using 14 and 15 primer sequences using PCR product synthesized as a template. As a result, PCR products consisting of 5'-XhoI-His6-linker (G3SG3TG3SG3)-eGFP-linker(G3SG3TG3SG3)-BamHI-3' and 5'-XhoI-His6-linker (G3SG3TG3SG3)-DsRed-linker(G3SG3TG3SG3)-BamHI-3' were obtained.

Six PCR products obtained from the above steps were successively inserted with pT7-7 vector to construct the expression vector that is able to synthesis HBV capsid-derived chimeric fluorescence nanoparticles (FIG. 22).

Example 8

Biosynthesis of HBV Capsid-Derived Chimeric Fluorescence Nanoparticles

Figure 23:
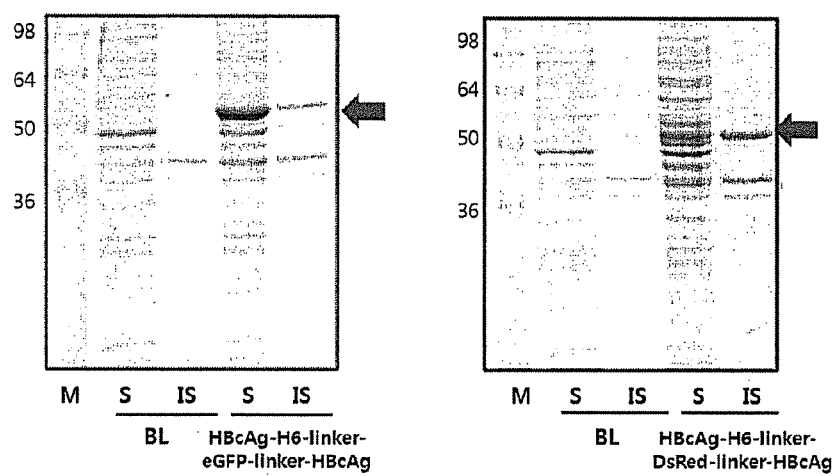
FIG. 23 shows an image showing the expression of recombinant protein.

*E. coli* strain BL21 (DE3) [F⁻ompThsdSB(rB⁻mB⁻)] was transformed with the expression vectors obtained from the above steps, respectively, and then ampicillin-resistant transformants were selected. The transformed *E coli* was incubated in the flask (250 mL Erlenmeyer flasks, 37° C., 150 rpm) containing 50 mL LB (Luria-Bertani) medium (contained with 100 mg $L^{-1}$). When the medium turbidity ($O.D_{600}$) was reached to about 0.6-0.7, IPTG (Isopropyl-β-D-thiogalactopyranoside) (0.7 mM) was added to induce the expression of recombinant gene. After incubating at 20° C. for 16~18 hours, *E. coli* was centrifuged at 4,500 rpm for 10 min to collect the bacterial precipitation; and then the precipitation was suspended to 5 ml sonication solution (10 mM Tris-HCl buffer solution, pH 7.5, 10 mM EDTA) and then sonicated by using Ultrasonic Homogenizer (Branson Ultrasonics Corp., Danbury, Conn., USA). After sonication, it was centrifuged at 13,000 rpm for 10 min, and then separated the supernatant from the insoluble aggregate. The supernatant and insoluble aggregate separated were separated and electrophoresed by using SDS-PAGE, and then stained to confirm of whether the recombinant protein was expressed. The expression of hydrosoluble recombinant protein was confirmed (FIG. 23).

Example 9

Purification of HBV Capsid-Derived Chimeric Fluorescence Nanoparticles

The purification of self-assembled fluorescence protein fusion protein nanoparticles among the recombinant proteins expressed as mentioned above was performed as the purification procedure of three steps as follows: 1) firstly, performing $Ni^{2+}$-NTA affinity chromatography using the binding of histidine and nickel that are fusion-expressed in the recombinant protein; 2) changing the solution containing the recombinant protein with other buffer (500 mM NaCl, 50 mM Tris-HCl pH 7.0) for self-assembling by using ultracentrifugal filter (Amicon Ultra 100K, Millipore, Billerica, Mass.) in order to improve the efficiency of self-assembling of the recombinant protein, and concentrating the recombinant protein at the same time; and 3) finally, performing sucrose gradient ultracentrifugation in order to separate only the self-assembled protein nanoparticles. The detailed explanation about each step are as follows:

1) $Ni^{2+}$-NTA Affinity Chromatography

*E. coli* incubated was collected with the same method as mentioned above in order to purify the recombinant protein; the obtained cell pellet was resuspended with 5 mL lysis buffer (pH 8.0, 50 mM sodium phosphate, 300 mM NaCl, 20 mM imidazole), and then the cell was sonicated by using Ultrosonic Homogenizer. The sonicated cell sap was centrifuged at 13,000 rpm for 10 min and the supernatant was separated, and then each recombinant protein was separated by using Ni2+-NTA column (Qiagen, Hilden, Germany) (Washing Buffer: pH 8.0, 50 mM sodium phosphate, 300 mM NaCl, 80 mM imidazole/Elution Buffer: pH 8.0, 50 mM sodium phosphate, 300 mM NaCl, 200 mM imidazole).

2) Changing Buffer and Concentrating for Promotion of Self-Assembly 3 ml recombinant protein eluted through $Ni^{2+}$-NTA affinity chromatography was placed to ultracentrifugal filter (Amicon Ultra 100K, Millipore, Billerica, Mass.) and centrifuged at 5,000 g for 10 min; and then the buffer (500 mM NaCl, 50 mM Tris-HCl pH 7.0) for self-assembly was filled in the top of column; centrifuged at 5,000 g until remaining 500 ul solution in the top of column; again filled with the buffer for self-assembly in the top of column; and then centrifuged. After repeating the above procedure three times, the buffer for self-assembly was changed with the solution for storing the recombinant protein.

3) Sucrose Gradient Ultracentrifuge

Figure 3:
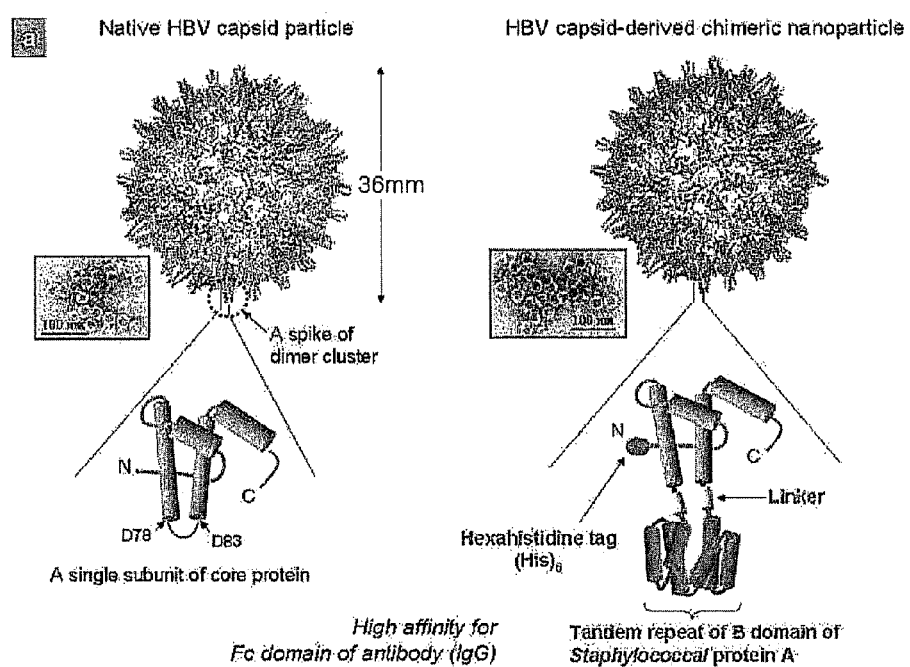
FIGS. 3 and 4 show three-dimensional diagnostic assay based on virus nanoparticles.
Figure 24:
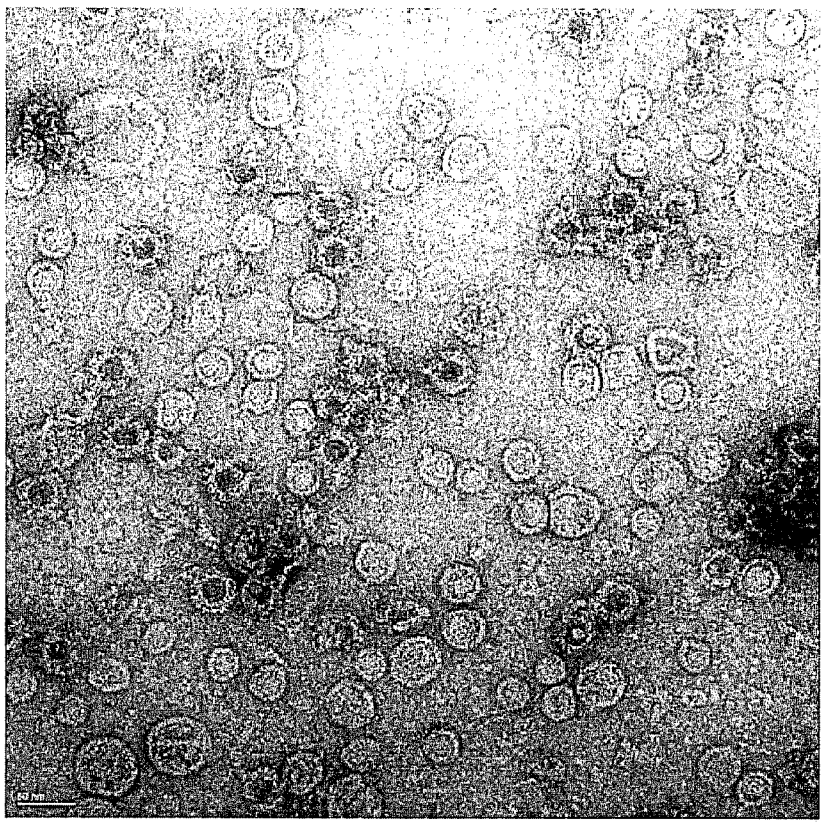
FIG. 24 shows TEM image confirming the formation of spherical nanoparticles with 30-35 nm size.

The solutions containing 60%, 50%, 40%, 30%, 20%, and 10% sucrose respectively were prepared by adding sucrose to the buffer for self-assembly by the concentrations, and then each of 2 ml sucrose solutions by the concentrations (60~20%) were put to tubes for the ultracentrifuge from the solution of high concentration. Finally, 0.5 ml of 10% sucrose solution was put; 1 ml solution of recombinant protein presented in the buffer for self-assembly already prepared was filled to the tubes; and then centrifuged at 24,000 rpm and 20° C. for 12 hours (Ultracentrifuge L-90k, Beckman). After centrifuging, the upper layer (10~30% sucrose solution part) was carefully removed by using a pipette and then the buffer of recombinant protein for 40~60% sucrose solution part was changed by using the buffer for self-assembly and ultracentrifugal filter as mentioned above 2). As a result, it was confirmed that the self-assembled spherical recombinant protein after centrifuging Sucrose Gradient Ultracentrifuge had high purity as compared with that after only $Ni^{2+}$-NTA affinity chromatography procedure as disclosed in FIG. 3 (FIG. 24).

Example 10

Structure Analysis of HBV Capsid-Derived Chimeric Fluorescence Nanoparticles Prepared The recombinant protein was taken a picture by using Transmission electron microscopy (TEM) in order to analyze the structure of recombinant protein nanoparticles purified as mentioned above. Firstly, the protein sample purified without a staining was dried after placing on the carbon-coated copper electron microscopy grids. In order to obtain the image of stained protein nanoparticles, the electron microscopy grids containing the air-drying sample was incubated at room temperature for 10 min along with 2% (v/v) aqueous uranyl acetate solution, and then washed 3-4 times with distilled water. The image of protein nanoparticles was observed by using Philips Technai 120 kV electron microscopy so that it was confirmed that it was spherical nanoparticles with 30-35 nm, and the result was disclosed in FIG. 24.

Example 11

Fluorescence Measurement of HBV Capsid-Derived Chimeric Fluorescence Nanoparticles Prepared The fluorescence intensities of four HBV capsid-derived chimeric fluorescence nanoparticles prepared according to the present invention [A) N-HBVcAg(1-78)-His6-eGFP-HBVcAg(81-149)-C, B) N-HBVcAg(1-78)-His6-DsRed-HBVcAg(81-149)-C, C) N-HBVcAg(1-78)-His6-linker-eGFP-linker-HBVcAg(81-149)-C and D) N-HBVcAg(1-78)-His6-linker-DsRed-linker-HBVcAg(81-149)-C] were measured. In order to compare the fluorescence intensity per a nanoparticle, eGFP monomer, DsRed monomer, and ferritin nanoparticle fusion fluorescence protein were prepared, respectively; 1 pmole (based on the protein nanoparticles) of eGFP monomer, DsRed monomer, and ferritin nanoparticle fusion fluorescence protein were put to black 96-well plate (Nunc, Roskide, Denmark) to measure the fluorescence. The fluorescence of eGFP monomer and eGFP fusion protein nanoparticle was measured at $\lambda_{ex}$=485 nm/$\lambda_{em}$=535 nm, and the fluorescence of DsRed and DsRed fusion protein nanoparticle was measured at $\lambda_{ex}$=550 nm/$\lambda_{em}$=590 nm using GENios (Tecan, Austria) three times, respectively. As a result, it was confirmed that the fluorescence intensity of HBcAg capsid fusion fluorescence protein was high as compared with that of monomer or ferritin fusion fluorescence protein due to the increase of fluorescence protein number expressed per protein nanoparticle, and also in the case of the insertion of linker, the distance between the fluorescence proteins was wide so that the effect of quenching was decreased and the fluorescence intensity was increased (FIG. 25).

TABLE 5

| Primer 1 | 5' NdeI-HBcAg1 | CATATG GACATTGACCCGTATAAAGA (Seq. No. 20) |
|---|---|---|
| Primer 2 | 3' XhoI-HBcAg78 | CTCGAG GTCTTCCAAATTACTTCCCA (Seq. No. 21) |
| Primer 3 | 5' BamHI-HBcAg81 | GGATCC TCCAGGGAATTAGTAGTCAGC (Seq. No. 22) |
| Primer 4 | 3' HindIII-HBcAg149 | AAGCTT TTAAACAACAGTAGTTTCCGGAAGTGT (Seq. No. 23) |
| Primer 5 | 5' XhoI-H6-eGFP | CTCGAG CATCACCATCACCATCAC GTGAGCAAGGGCGAG (Seq. No. 24) |
| Primer 6 | 3' BamHI-eGFP | GGATCC CTTGTACAGCTCGTCCATGCC (Seq. No. 25) |
| Primer 7 | 5' XhoI-H6-DsRed | CTCGAG CATCACCATCACCATCAC GACAACACCGAGGAC (Seq. No. 26) |
| Primer 8 | 3' BamHI-DsRed | GGATCC CTGGGAGCCGGAGTGGCG (Seq. No. 27) |
| Primer 9 | 5' linkerN-eGFP | GGCTCTGGTGGCGGAAGTGGGGGTGGC GTGAGCAAGGGCGAG (Seq. No. 28) |
| Primer 10 | 3' linklerC-eGFP | AGAGCCACCCCCACTTCCGCCACC CTTGTACAGCTCGTCCAT (Seq. No. 29) |
| Primer 11 | 5' linkerN-DsRed | GGCTCTGGTGGCGGAAGTGGGGGTGGC GACAACACCGAGGAC (Seq. No. 30) |
| Primer 12 | 3' linkerC-DsRed | AGAGCCACCCCCACTTCCGCCACC CTGGGAGCCGGAGTGGCG (Seq. No. 31) |
| Primer 13 | 5' XhoI-Hs-linkerN1 | GGTGGCGGAAGTGGG GGTGGCTCTGGTGGCGAAGT (Seq. No. 32) |
| Primer 14 | 5' XhoI-Hs-linkerN2 | CTCGAG CATCACCATCACCATCAC GGTGGCGGAAGTGGG (Seq. No. 33) |
| Primer 15 | 3' BamHI-linker | CGGATCC GCCACCCCC ACTTCCGCCACC AGAGCCACCCCCACT (Seq. No. 34) |

Table 5 shows the information about Primers (5' to 3').

The invention has been described in detail with reference to embodiments thereof. However, it will be appreciated by those skilled in the art that changes may be made in these embodiments without departing from the principles and spirit of the invention, the scope of which is defined in the appended claims and their equivalents.

What is claimed is:

1. A substrate for detecting a disease marker including a solid surface upon which is immobilized a chimeric Hepatitis B virus (HBV) capsid comprising one or more tandem repeats of B domain of Staphylococcal protein A ($SPA_B$) and a subunit protein of HBV capsid.

2. The substrate according to claim 1, wherein the chimeric HBV capsid comprises:

(1) amino acid 1 to 78 of the subunit protein of HBV capsid;

(2) one or more tandem repeats of $SPA_B$; and (3) amino acids 81 to 149 of the subunit protein of HBV capsid.

3. The substrate according to claim 1, wherein the substrate is used as a nanosensor.

4. The substrate according to claim 1, wherein the solid surface is selected from the group consisting of silicon, Langmuir-Blodgett film, functionalized glass, germanium, ceramics, silicon, semiconductor raw material, polytetrafluoroethylene (PTFE), carbon, polycarbonate, mica, Mylar, poly vinylidene fluoride (PVDF), plastic, quartz, polystyrene, gallium arsenide, gold, silver, metal, metal alloy, fabric, and their combinations capable of having functional group, such as amino, carboxyl, thiol or hydroxyl that are incorporated on the their surfaces.

5. The substrate according to claim 4, wherein the metal includes a nickel nano structure.

6. A nanosensor fabricated by binding an antibody capable of recognizing a disease marker with the immobilized chimeric HBV capsid according to claim 1, thereby immobilizing the antibody to the surface of the chimeric HBV capsid and producing a nanosensor having a three-dimensional nanostructure.

7. A method for detecting a disease marker in a sample, comprising contacting the sample with the nanosensor according to claim 6 and determining whether the antibody in the nanosenser binds the disease marker.

8. The method according to claim 7, wherein the sample is blood, serum, urea, saliva, sputum or nasal discharge.

9. The method according to claim 7, wherein the disease marker is Troponin I or an enterotoxin.

10. The substrate according to claim 1, comprising two tandem repeats of $SPA_B$.

11. The substrate according to claim 1, comprising a Hexahistidine $(His)_6$ tag.

12. The substrate according to claim 1, comprising a biotinylated peptide.

13. The substrate according to claim 12, wherein the biotinylated peptide has a sequence of SEQ ID NO: 17.

14. The substrate according to claim 2, wherein the amino acids 1 to 78 of the subunit protein of HBV capsid has a sequence of SEQ ID NO: 13, the one or more tandem repeats of $SPA_B$ has a sequence of SEQ ID NO: 16, and the amino acids 81 to 149 of the subunit protein of HBV capsid has a sequence of SEQ ID NO: 15.

* * * * *